(12) United States Patent
Gale et al.

(10) Patent No.: US 9,517,149 B2
(45) Date of Patent: Dec. 13, 2016

(54) BIODEGRADABLE STENT WITH ENHANCED FRACTURE TOUGHNESS

(71) Applicant: Abbott Cardiovascular Systems Inc., Santa Clara, CA (US)

(72) Inventors: David C. Gale, Kennesaw, GA (US); Bin Huang, Pleasanton, CA (US); Stephen Schaible, Anaheim, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/998,199

(22) Filed: Oct. 9, 2013

(65) Prior Publication Data

US 2014/0107762 A1  Apr. 17, 2014

Related U.S. Application Data

(60) Continuation-in-part of application No. 12/845,536, filed on Jul. 28, 2010, now Pat. No. 8,658,081, which
(Continued)

(51) Int. Cl.
*A61F 2/90* (2013.01)
*A61F 2/82* (2013.01)
(Continued)

(52) U.S. Cl.
CPC . *A61F 2/90* (2013.01); *A61F 2/82* (2013.01); *A61F 2/91* (2013.01); *A61F 2/915* (2013.01); *A61L 31/06* (2013.01); *A61L 31/14* (2013.01); *B29C 49/0005* (2013.01); *B29C 55/24* (2013.01); *B29C 69/001* (2013.01); *A61F 2002/91533* (2013.01); *A61F 2002/91558* (2013.01); *A61F 2002/91566* (2013.01); *A61F 2002/91575* (2013.01); *A61F 2002/9522* (2013.01); *B29C 35/045* (2013.01); *B29C 49/14* (2013.01); *B29C 49/4823* (2013.01); *B29C 2049/0089* (2013.01);
(Continued)

(58) Field of Classification Search
None
See application file for complete search history.

(56) References Cited

U.S. PATENT DOCUMENTS

| 3,636,956 A | 1/1972 | Schneider |
| 4,136,143 A | 1/1979 | Lupke et al. |

(Continued)

FOREIGN PATENT DOCUMENTS

| EP | 0 583 170 | 2/1994 |
| EP | 1184008 | 3/2002 |

(Continued)

OTHER PUBLICATIONS

International Search Report for PCT/US2005/025759 filed Jul. 20, 2005, mailed Dec. 27, 2005, 15 pgs.
(Continued)

*Primary Examiner* — Thomas J Sweet
*Assistant Examiner* — Megan Wolf
(74) *Attorney, Agent, or Firm* — Squire Patton Boggs (US) LLP

(57) ABSTRACT

Stents and methods of manufacturing a stents with enhanced fracture toughness are disclosed.

4 Claims, 21 Drawing Sheets
(16 of 21 Drawing Sheet(s) Filed in Color)

Related U.S. Application Data is a continuation of application No. 12/772,698, filed on May 3, 2010, now Pat. No. 8,323,329, which is a division of application No. 11/454,968, filed on Jun. 15, 2006, now Pat. No. 7,731,890, application No. 13/998,199, which is a continuation-in-part of application No. 13/112,960, filed on May 20, 2011, which is a continuation-in-part of application No. 11/443,947, filed on May 30, 2006, now Pat. No. 7,971,333, application No. 13/998,199, which is a continuation-in-part of application No. 13/463,562, filed on May 3, 2012, now Pat. No. 8,715,564, which is a division of application No. 12/806,785, filed on Aug. 19, 2010, now Pat. No. 8,192,678, which is a division of application No. 10/899,948, filed on Jul. 26, 2004, now abandoned, application No. 13/998,199, which is a continuation-in-part of application No. 11/444,596, filed on May 31, 2006, now Pat. No. 8,747,879, which is a continuation-in-part of application No. 11/413,220, filed on Apr. 28, 2006, now Pat. No. 8,747,878, application No. 13/998,199, which is a continuation-in-part of application No. 10/956,910, filed on Sep. 30, 2004, now Pat. No. 8,778,256, and a continuation-in-part of application No. 13/597,161, filed on Aug. 28, 2012, now Pat. No. 8,658,082, which is a continuation-in-part of application No. 12/001,777, filed on Dec. 11, 2007, now Pat. No. 8,268,228, application No. 13/998,199, which is a continuation-in-part of application No. 13/734,879, filed on Jan. 4, 2013, now Pat. No. 9,211,682, which is a continuation-in-part of application No. 12/559,400, filed on Sep. 14, 2009, now Pat. No. 8,501,079, application No. 13/998,199, which is a continuation-in-part of application No. 12/558,105, filed on Sep. 11, 2009, now abandoned, and a continuation-in-part of application No. 12/490,248, filed on Jun. 23, 2009, now Pat. No. 8,597,716, and a continuation-in-part of application No. 13/631,061, filed on Sep. 28, 2012, now Pat. No. 8,828,305, which is a division of application No. 13/192,315, filed on Jul. 27, 2011, now Pat. No. 8,303,296, which is a continuation of application No. 12/424,484, filed on Apr. 15, 2009, now Pat. No. 8,012,402.

(60) Provisional application No. 61/086,100, filed on Aug. 4, 2008, provisional application No. 61/095,617, filed on Sep. 9, 2008.

(51) Int. Cl.
    *A61F 2/915* (2013.01)
    *A61L 31/06* (2006.01)
    *A61L 31/14* (2006.01)
    *B29C 49/00* (2006.01)
    *B29C 55/24* (2006.01)
    *B29C 69/00* (2006.01)
    *A61F 2/91* (2013.01)
    *A61F 2/95* (2013.01)
    *B29C 35/04* (2006.01)
    *B29C 49/14* (2006.01)
    *B29C 49/48* (2006.01)
    *B29K 67/00* (2006.01)
    *B29K 105/00* (2006.01)
    *B29L 31/00* (2006.01)

(52) U.S. Cl.
    CPC .. *B29C 2793/0009* (2013.01); *B29K 2067/00* (2013.01); *B29K 2067/046* (2013.01); *B29K 2105/258* (2013.01); *B29K 2995/006* (2013.01); *B29L 2031/7534* (2013.01)

(56) References Cited

U.S. PATENT DOCUMENTS

| | | |
|---|---|---|
| 4,547,416 A | 10/1985 | Reed et al. |
| 4,698,196 A | 10/1987 | Fabian et al. |
| 4,702,884 A | 10/1987 | Goldstein |
| 4,957,687 A | 9/1990 | Akman et al. |
| 4,987,025 A | 1/1991 | Shiraki et al. |
| 5,087,394 A | 2/1992 | Keith |
| 5,108,416 A | 4/1992 | Ryan et al. |
| 5,116,365 A | 5/1992 | Hillstead |
| 5,147,302 A | 9/1992 | Euteneuer et al. |
| 5,342,348 A | 8/1994 | Kaplan |
| 5,500,013 A | 3/1996 | Buscemi et al. |
| 5,514,154 A | 5/1996 | Lau et al. |
| 5,591,230 A | 1/1997 | Horn et al. |
| 5,628,786 A | 5/1997 | Banas et al. |
| 5,670,161 A | 9/1997 | Healy et al. |
| 5,725,547 A | 3/1998 | Chuter |
| 5,741,327 A | 4/1998 | Frantzen |
| 5,780,807 A | 7/1998 | Saunders |
| 5,843,164 A | 12/1998 | Frantzen et al. |
| 5,868,782 A | 2/1999 | Frantzen |
| 5,891,386 A | 4/1999 | Deitermann et al. |
| 5,906,759 A | 5/1999 | Richter |
| 5,922,005 A | 7/1999 | Richter et al. |
| 5,925,061 A | 7/1999 | Ogi |
| 5,928,280 A | 7/1999 | Hansen et al. |
| 6,033,434 A | 3/2000 | Borghi et al. |
| 6,042,606 A | 3/2000 | Frantzen |
| 6,083,259 A | 7/2000 | Frantzen |
| 6,206,911 B1 | 3/2001 | Milo |
| 6,273,910 B1 | 8/2001 | Limon |
| 6,283,990 B1 | 9/2001 | Kanesaka |
| 6,312,459 B1 | 11/2001 | Huang et al. |
| 6,360,577 B2 | 3/2002 | Austin |
| 6,423,092 B2 | 7/2002 | Datta et al. |
| 6,500,146 B1 | 12/2002 | Pinchuk et al. |
| 6,530,950 B1 | 3/2003 | Alvarado et al. |
| 6,558,415 B2 | 5/2003 | Thompson |
| 6,572,813 B1 | 6/2003 | Zhang et al. |
| 6,613,079 B1 * | 9/2003 | Wolinsky et al. ........... 623/1.15 |
| 6,616,689 B1 | 9/2003 | Ainsworth et al. |
| 6,626,939 B1 | 9/2003 | Burnside et al. |
| 6,629,994 B2 | 10/2003 | Gomez et al. |
| 6,634,426 B2 | 10/2003 | McCoy et al. |
| 6,638,300 B1 | 10/2003 | Frantzen |
| 6,645,422 B2 | 11/2003 | Jung et al. |
| 6,758,859 B1 | 7/2004 | Dang et al. |
| 6,852,124 B2 | 2/2005 | Cox et al. |
| 6,997,944 B2 | 2/2006 | Harrison et al. |
| 6,997,946 B2 | 2/2006 | Girton et al. |
| 7,066,952 B2 | 6/2006 | Igaki |
| 7,070,615 B1 | 7/2006 | Igaki |
| 7,083,639 B2 | 8/2006 | Guinan et al. |
| 7,115,691 B2 | 10/2006 | Alvarado et al. |
| 7,128,868 B2 | 10/2006 | Eidenschink |
| 7,273,492 B2 | 9/2007 | Cheng et al. |
| 7,273,495 B2 | 9/2007 | Limon |
| 7,374,570 B2 | 5/2008 | Alvarado et al. |
| 7,637,886 B2 | 12/2009 | Herweck et al. |
| 7,666,342 B2 | 2/2010 | Limon et al. |
| 7,731,740 B2 | 6/2010 | LaFont et al. |
| 7,731,890 B2 | 6/2010 | Gale et al. |
| 7,761,968 B2 | 7/2010 | Huang et al. |
| 7,763,066 B2 | 7/2010 | Parker |
| 7,887,579 B2 | 2/2011 | Mangiardi et al. |
| 7,971,333 B2 | 7/2011 | Gale et al. |
| 8,002,817 B2 | 8/2011 | Limon |
| 8,043,553 B1 | 10/2011 | Durcan |
| 8,099,849 B2 | 1/2012 | Gale et al. |
| 8,173,062 B1 | 5/2012 | Durcan |
| 8,192,678 B2 | 6/2012 | Huang et al. |

(56) References Cited

U.S. PATENT DOCUMENTS

| | | |
|---|---|---|
| 8,206,436 B2 | 6/2012 | Mangiardi et al. |
| 8,211,163 B2 | 7/2012 | Dakin et al. |
| 8,241,554 B1 | 8/2012 | Abbate et al. |
| 8,252,215 B2 | 8/2012 | Wang |
| 8,261,423 B2 | 9/2012 | Jow et al. |
| 8,303,296 B2 | 11/2012 | Kleiner et al. |
| 8,303,644 B2 | 11/2012 | Lord et al. |
| 8,303,645 B2 | 11/2012 | Oepen et al. |
| 8,323,329 B2 | 12/2012 | Gale et al. |
| 8,388,673 B2 | 3/2013 | Yang et al. |
| 8,539,663 B2 | 9/2013 | Wang et al. |
| 2001/0014821 A1 | 8/2001 | Juman et al. |
| 2001/0020184 A1 | 9/2001 | Dehdashtian et al. |
| 2002/0035394 A1 | 3/2002 | Fierens et al. |
| 2002/0041059 A1 | 4/2002 | Jung et al. |
| 2002/0077592 A1 | 6/2002 | Barry |
| 2002/0099438 A1 | 7/2002 | Furst |
| 2002/0107562 A1 | 8/2002 | Hart |
| 2002/0138133 A1 | 9/2002 | Lenz et al. |
| 2002/0151965 A1 | 10/2002 | Roth |
| 2002/0183716 A1* | 12/2002 | Herweck et al. ............. 604/509 |
| 2003/0009151 A1 | 1/2003 | Wang |
| 2003/0023301 A1 | 1/2003 | Cox et al. |
| 2003/0028241 A1 | 2/2003 | Stinson |
| 2003/0028246 A1 | 2/2003 | Palmaz et al. |
| 2003/0050687 A1 | 3/2003 | Schwade et al. |
| 2003/0055488 A1 | 3/2003 | Igaki |
| 2003/0083732 A1 | 5/2003 | Stinson |
| 2003/0088310 A1 | 5/2003 | Hansen et al. |
| 2003/0149470 A1 | 8/2003 | Alvarado et al. |
| 2003/0187158 A1 | 10/2003 | Preuschen et al. |
| 2003/0208254 A1 | 11/2003 | Shortt |
| 2003/0226833 A1 | 12/2003 | Shapovalov et al. |
| 2004/0000361 A1 | 1/2004 | Trozera |
| 2004/0044400 A1 | 3/2004 | Cheng et al. |
| 2004/0098090 A1 | 5/2004 | Williams et al. |
| 2004/0181271 A1 | 9/2004 | DeSimone et al. |
| 2004/0215326 A1 | 10/2004 | Goodson et al. |
| 2005/0004656 A1 | 1/2005 | Das |
| 2005/0004659 A1 | 1/2005 | Von Oepen et al. |
| 2005/0004662 A1 | 1/2005 | Von Oepen et al. |
| 2005/0004663 A1 | 1/2005 | Llanos et al. |
| 2005/0102022 A1 | 5/2005 | Solovay et al. |
| 2005/0137678 A1 | 6/2005 | Varma |
| 2005/0149172 A1 | 7/2005 | Varma |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2005/0203617 A1 | 9/2005 | Forster et al. |
| 2006/0020330 A1 | 1/2006 | Huang et al. |
| 2006/0058863 A1 | 3/2006 | LaFont et al. |
| 2006/0076708 A1 | 4/2006 | Huang et al. |
| 2006/0095115 A1 | 5/2006 | Bladillah et al. |
| 2006/0136040 A1 | 6/2006 | Burgermeister et al. |
| 2006/0193893 A1 | 8/2006 | Brown |
| 2006/0211952 A1 | 9/2006 | Kennedy |
| 2006/0224226 A1 | 10/2006 | Huang et al. |
| 2006/0235506 A1 | 10/2006 | Ta et al. |
| 2006/0259122 A1 | 11/2006 | Eliseev |
| 2006/0265050 A1 | 11/2006 | Morris et al. |
| 2007/0038290 A1 | 2/2007 | Huang et al. |
| 2007/0073016 A1 | 3/2007 | Alvarado et al. |
| 2007/0073376 A1 | 3/2007 | Krolik et al. |
| 2007/0135892 A1 | 6/2007 | Burgermeister et al. |
| 2007/0135896 A1 | 6/2007 | Burgermeister et al. |
| 2007/0135898 A1 | 6/2007 | Burgermeister et al. |
| 2007/0135899 A1 | 6/2007 | Burgermeister et al. |
| 2007/0135983 A1 | 6/2007 | McDonald et al. |
| 2007/0135985 A1 | 6/2007 | Berry et al. |
| 2007/0156226 A1 | 7/2007 | Chew et al. |
| 2007/0200229 A1 | 8/2007 | Daubenspeck et al. |
| 2007/0213810 A1 | 9/2007 | Newhauser et al. |
| 2007/0216619 A1 | 9/2007 | Hung |
| 2007/0253996 A1 | 11/2007 | Huang et al. |
| 2007/0253999 A1 | 11/2007 | Huang et al. |
| 2007/0265698 A1 | 11/2007 | Pienknagura |
| 2007/0271763 A1 | 11/2007 | Huang et al. |
| 2007/0282431 A1 | 12/2007 | Gale et al. |
| 2007/0282433 A1 | 12/2007 | Limon et al. |
| 2007/0283552 A1 | 12/2007 | Gale et al. |
| 2007/0290412 A1 | 12/2007 | Capek et al. |
| 2007/0293938 A1 | 12/2007 | Gale et al. |
| 2008/0001333 A1 | 1/2008 | Kleine et al. |
| 2008/0147164 A1 | 6/2008 | Gale et al. |
| 2008/0177373 A1 | 7/2008 | Huang et al. |
| 2008/0177374 A1 | 7/2008 | Zheng et al. |
| 2008/0275537 A1 | 11/2008 | Limon |
| 2008/0300670 A1 | 12/2008 | Gueriguian et al. |
| 2008/0312727 A1 | 12/2008 | Blank |
| 2009/0001633 A1 | 1/2009 | Limon et al. |
| 2009/0005854 A1 | 1/2009 | Huang et al. |
| 2009/0005860 A1 | 1/2009 | Huang et al. |
| 2009/0012598 A1 | 1/2009 | Abbate et al. |
| 2009/0146348 A1 | 6/2009 | Huang et al. |
| 2009/0216311 A1 | 8/2009 | Flagle et al. |
| 2009/0264979 A1 | 10/2009 | Kao et al. |
| 2010/0004735 A1 | 1/2010 | Yang et al. |
| 2010/0025894 A1 | 2/2010 | Kleiner et al. |
| 2010/0174358 A1 | 7/2010 | Rabkin et al. |
| 2010/0204778 A1 | 8/2010 | LaFont et al. |
| 2010/0217373 A1 | 8/2010 | Boyle et al. |
| 2010/0256736 A1 | 10/2010 | Purdy et al. |
| 2010/0256740 A1 | 10/2010 | Limon et al. |
| 2010/0274349 A1 | 10/2010 | Lord et al. |
| 2010/0289191 A1 | 11/2010 | Gale et al. |
| 2010/0323091 A1 | 12/2010 | Castro et al. |
| 2011/0066222 A1 | 3/2011 | Wang et al. |
| 2011/0112627 A1 | 5/2011 | Gale et al. |
| 2011/0172759 A1 | 7/2011 | Schmid et al. |
| 2011/0190871 A1 | 8/2011 | Trollsas et al. |
| 2011/0190872 A1 | 8/2011 | Anukhin et al. |
| 2011/0224778 A1 | 9/2011 | Gale et al. |
| 2011/0230959 A1 | 9/2011 | Pienknagura |
| 2011/0245904 A1 | 10/2011 | Pacetti et al. |
| 2011/0260352 A1 | 10/2011 | Tang et al. |
| 2011/0270383 A1 | 11/2011 | Jow et al. |
| 2011/0270384 A1 | 11/2011 | Lord |
| 2011/0271513 A1 | 11/2011 | Wang |
| 2011/0278771 A1 | 11/2011 | Kleiner et al. |
| 2012/0042501 A1 | 2/2012 | Wang et al. |
| 2012/0073733 A1 | 3/2012 | Ngo et al. |
| 2012/0271396 A1 | 10/2012 | Zheng et al. |
| 2012/0285609 A1 | 11/2012 | Wang |
| 2012/0299226 A1 | 11/2012 | Wang et al. |
| 2012/0316635 A1 | 12/2012 | Jow et al. |
| 2012/0319333 A1 | 12/2012 | Huang et al. |
| 2012/0330403 A1 | 12/2012 | Gomez et al. |
| 2013/0026681 A1 | 1/2013 | Kleiner et al. |
| 2013/0150943 A1 | 6/2013 | Zheng et al. |
| 2013/0181380 A1 | 7/2013 | Yang et al. |
| 2013/0255853 A1 | 10/2013 | Wang et al. |

FOREIGN PATENT DOCUMENTS

| | | |
|---|---|---|
| EP | 1 800 628 | 6/2007 |
| EP | 1 859 823 | 11/2007 |
| EP | 2 152 207 | 11/2008 |
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |
| WO | WO 2007/021706 | 2/2007 |
| WO | WO 2007/142750 | 12/2007 |
| WO | WO 2007/146354 | 12/2007 |
| WO | WO 2007/149457 | 12/2007 |

OTHER PUBLICATIONS

Answers.com blow molding; retrieved from www.answers.com/blow%20molding#Stretch_blow_molding, Jun. 26, 2009, 11 pgs.

(56) References Cited

OTHER PUBLICATIONS www.engineeringtoolbox.com/thermal/conductivity/d_429.html., Jun. 26, 2009, 4 pgs.

Kalish et al., "Spectroscopic and thermal analyses of α' and α crystalline forms of poly (L-lactic acid)", Polymer 52, pp. 814-821 (2011).

Seguela et al., "Strain-Induced Molecular Ordering in Polylactide upon Uniaxial Stretching", Macromolecules 43, pp. 1488-1498 (2010).

White et al., "Specification of Biaxial Orientation in Amorphous and Crystalline Polymers", Polymer Engineering and Science vol. 21, No. 13, pp. 859-868 (1981).

Zhang et al., "Confirmation of Disorder α Form of Poly (L-lactic acid) by the X-ray Fiber Pattern and Polarized IR/Raman Spectra Measured for Uniaxially-Oriented Samples", Macromol. Symp. 242, pp. 274-278 (2006).

Zhang et al., "Structure variation of tensile-deformed amorphous poly(L-lactic acid):Effects of deformation rate and strain", Polymer 52, pp. 4141-4149 (2011).

Cocca et al., "Influence of crystal polymorphism on mechanical and barrier properties of poly (L-lactic acid)", Eur. Polym. J. 9 pgs. (2011).

Zhang et al., "Disorder-to-Order Phase Transition and Multiple Melting Behavior of Poly(L-lactide) Investigated by Simultaneous Measurements of WAXD and DSC", Macromolecules 41, pp. 1352-1357 (2008).

U.S. Appl. No. 10/956,910, Sep. 30, 2004, Huang et al.

Declaration under 37 C.F.R. § 1.132 by Bin Huang and David Gale filed in U.S. Appl. No. 11/417,376, executed Jul. 22, 2010, 5 pgs.

Answers.com blow molding; retrieved fro www.answers.com/blow%20molding;πStretch_blow_molding, Jun. 26, 2009, 11 pgs.

International Search Report for PCT/US2007/013915 filed Jun. 13, 2007, mailed Jan. 7, 2008, 4 pgs.

Middleton et al., Synthetic Industry; downloaded from: devices, Mar. 1998, Biodegradable Polymers as Medical Devices, Medical Device and Diagnostic www.mddionline.com/article/synthetic-biodegradable-polymers-medical-devices, Mar. 1998, 4 pgs.

Angioplasty Summit Abstracts/Oral, The Am. J. o Cardiology, Apr. 23-26, 2013, p. 23B.

Bosiers et al., "Coronary and endovascular applications of the Absorb™ bioresorbable vascular scaffold", Interv. Cardiol. 4(6), pp. 621-631 (2012).

Miller "Abbott's Bioresorbable Stent Shows Durable Results in Absorb Trial", The Gray Sheet, pp. 17-18, Mar. 2003.

International Search Report for PCT/US2008/062607, mailed Aug. 5, 2008, 6 pgs.

European Search Report for appl. No. 08 747619.8, mailed Sep. 27, 2011, 5 pgs.

Translation of Notice of Reason for Rejection for JP appl. No. 2010-506710, dispatched Sep. 25, 2012, 3 pgs.

\* cited by examiner

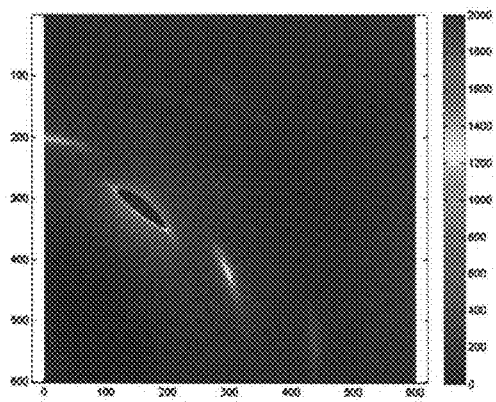
FIG. 22D
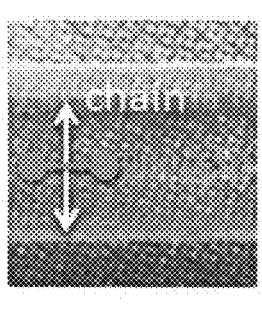 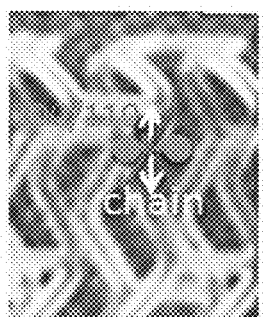 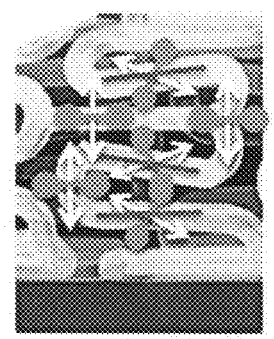 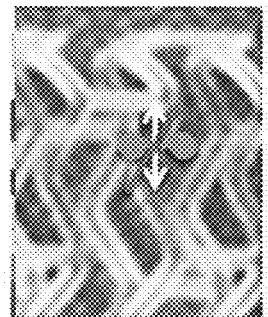
FIG. 23A      FIG. 23B      FIG. 23C      FIG. 23D

BIODEGRADABLE STENT WITH ENHANCED FRACTURE TOUGHNESS

CROSS-REFERENCE TO RELATED APPLICATIONS

This application is a continuation-in-part of application Ser. No. 13/463,562 filed May 3, 2012, now U.S. Pat No. 8,715,564, which is a divisional of application Ser. No. 12/806,785, filed Aug. 19, 2010, now U.S. Pat. No. 8,192,678, which is a divisional of application Ser. No. 10/899,948, filed Jul. 26, 2004, now abandoned, all of which is incorporated herein by reference for all purposes.

This application is also a continuation-in-part of U.S. application Ser. No. 13/112,960 filed May 20, 2011 which is a continuation of U.S. application Ser. No. 11/443,947 filed on May 30, 2006, now U.S. Pat. No. 7,971,333, all of which are incorporated by reference herein for all purposes.

This is a continuation-in-part of U.S. patent application Ser. No. 11/444,596 filed May 31, 2006, now U.S. Pat. No. 8,747,879, which is a continuation in part of application Ser. No. 11/413,220 filed Apr. 28, 2006, now U.S. Pat. No. 8,747,878, all of which are incorporated by reference herein for all purposes.

This is also a continuation-in-part of application Ser. No. 12/845,536 filed on Jul. 28, 2010, , now U.S. Pat. No. 8,658,081, which is a continuation of application Ser. No. 12/772,698 filed on May 3, 2010, now U.S. Pat. No. 8,323,329, which is a divisional application of Ser. No. 11/454,968 filed on Jun. 15, 2006, now U.S. Pat. No. 7,731,890, all of which are incorporated by reference herein for all purposes.

This is also a continuation-in-part of application Ser. No. 10/956,910 filed on Sep. 30, 2004, now U.S. Pat. No. 8,778,256, which is incorporated by reference herein for all purposes.

This is also a continuation-in-part of U.S. patent application Ser. No. 13/597,161 filed Aug. 28, 2012, now U.S. Pat. No. 8,658,082, which is a continuation of application Ser. No. 12/001,777 filed Dec. 11, 2007, now U.S. Pat. No. 8,268,228, all of which are incorporated by reference herein for all purposes.

This application is also a continuation-in-part of U.S. application Ser. No. 13/734,879 filed Jan. 4, 2013, now U.S. Pat. No. 9,211,682, which is a continuation of U.S. application Ser. No. 12/559,400 filed Sep. 14, 2009, now U.S. Pat. No. 8,501,079, all of which are incorporated by reference herein for all purposes.

This application is also a continuation-in-part of U.S. application Ser. No. 12/558,105 filed Sep. 11, 2009, now abandoned, which is incorporated by reference herein for all purposes.

This application is also a continuation-in-part of U.S. application Ser. No. 12/490,248 filed Jun. 23, 2009, now U.S. Pat. No. 8,597,716, which is incorporated by reference herein for all purposes.

This application is also a continuation-in-part of application Ser. No. of 13/631,061 filed Sep. 28, 2012, now U.S. Pat. No. 8,828,305, which is a divisional of application Ser. No. 13/192,315, now U.S. Pat. No. 8,303,296,which is incorporated by reference herein, which was filed on Jul. 27, 2011 which is a continuation of application Ser. No. 12/424,484, now U.S. Pat. No. 8,012,402, which is incorporated by reference herein, which claims benefit of U.S. Patent Application No. 61/086,100, which was filed on Aug. 4, 2008 and claims benefit of U.S. Patent Application No. 61/095,617, which was filed on Sep. 9, 2008, which is incorporated by reference herein.

BACKGROUND OF THE INVENTION

Field of the Invention

This invention relates to methods of fabricating stents having selected mechanical properties.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

SUMMARY OF THE INVENTION

Certain embodiments of the present invention include a stent comprising a cylindrically aligned bending element formed by a first bar arm and a second bar arm, the angle between the bar arms being greater than about 90°, wherein the stent is fabricated from a tube radially expanded by at least about 400%.

Further embodiments of the present invention include a stent comprising a cylindrically aligned bending element formed by a first bar arm and a second bar arm, an angle between each of the bar arms and the circumferential direction being less than about 45°, wherein the stent is fabricated from a tube radially expanded by at least 500%.

Additional embodiments of the present invention include a stent comprising a plurality of cylindrically aligned bending elements, the angles between the bending elements being greater than about 90°.

Other embodiments of the present invention include a method of fabricating a stent comprising: radially expanding a tube to at least about 400%; and cutting a pattern comprising a cylindrically aligned bending element formed by a first bar arm and a second bar arm, the angle between the bar arms being greater than about 90°, wherein the stent is fabricated from a tube radially expanded by at least about 400%.

Some embodiments of the present invention include a method for fabricating a stent comprising: conveying a gas into a poly(L-lactide) tube disposed within a cylindrical mold to increase a pressure inside the tube, wherein the increased pressure radially expands the polymeric tube to conform to the inside surface of the mold; applying tension along the axis of the tube to axially extend the tube; and fabricating a stent from the radially expanded and axially extended tube.

Certain embodiment of the present invention include a method for fabricating a stent comprising: processing a polymer form to increase the Tg of the polymer at least about 10° C.; and fabricating a stent from the processing form.

Additional embodiments of the present invention include a method for fabricating a stent comprising: processing a polymer form so as to increase the Tg of the polymer to at least about 40° C. above ambient temperature to allow storage of the processed polymer at the ambient temperature; and fabricating a stent from the processed polymer.

Other embodiments of the present invention include a method for fabricating a stent comprising: processing a polymer form so as to increase the Tg of the polymer to at least about 20° C. above a crimping temperature.

The present invention includes one or more of the following thirteen embodiments or any combination of the following thirteen embodiments:

Embodiment one includes a biodegradable stent comprising: a scaffold comprising a poly(L-lactide)-based biodegradable polymer including crystal domains and amorphous domains, wherein the crystal domains comprise α' morphology crystal structures, and wherein the scaffold is radially expandable to a deployed state in a blood vessel of a body to hold open the blood vessel.

The stent of embodiment one, wherein the crystal domains comprise mostly α' morphology crystal structure.

The stent of embodiment one, wherein the crystal domains comprise only α' morphology crystal structure.

The stent of embodiment one, wherein the crystal domains comprise only α' morphology crystal structure in a fabricated state.

The stent of embodiment one, wherein the crystal domains comprise only α' morphology crystal structure in a crimped state.

The stent of embodiment one, wherein the crystal domains comprise only α' morphology crystal structure in the deployed state.

The stent of embodiment one, wherein the crystal domains comprise a morphology crystal structure.

The stent of embodiment one, wherein the scaffold comprises an uncrimped state and a crimped state, wherein only α' crystal structure is detectable by WAXD in the uncrimped state, the crimped state, and the deployed state.

The stent of embodiment one, wherein the scaffold comprises an uncrimped state and a crimped state, wherein only α' crystal structure is detectable by WAXD in the uncrimped state.

The stent of embodiment one, wherein the scaffold comprises a crimped state, wherein only α' crystal structure is detectable by WAXD in the crimped state.

The stent of embodiment one, wherein only α' crystal structure is detectable by WAXD in the deployed state.

Embodiment two includes a biodegradable stent comprising: a scaffold including a pattern of struts formed into a tube, wherein the tube has been processed to increase crystallinity prior to forming the pattern, wherein the scaffold comprises a poly(L-lactide)-based biodegradable polymer including crystal domains and amorphous domains, wherein the crystal domains comprise α' morphology crystal structures, and wherein the scaffold is radially expandable in a blood vessel of a body to a deployed state to hold open the blood vessel.

The stent of embodiment two, wherein the crystal domains comprise mostly α' morphology crystal structure.

The stent of embodiment two, wherein the crystal domains comprise only α' morphology crystal structure.

The stent of embodiment two, wherein the crystal domains comprise only α' morphology crystal structure in a fabricated state.

The stent of embodiment two, wherein the crystal domains comprise only α' morphology crystal structure in a crimped state.

The stent of embodiment two, wherein the crystal domains comprise only α' morphology crystal structure in the deployed state.

The stent of embodiment two, wherein the crystal domains comprise a morphology crystal structure.

The stent of embodiment two, wherein the scaffold comprises an uncrimped state and a crimped state, wherein only α' crystal structure is detectable by WAXD in the uncrimped state, the crimped state, and the deployed state.

The stent of embodiment two, wherein the scaffold comprises an uncrimped state and a crimped state, wherein only α' crystal structure is detectable by WAXD in the uncrimped state.

The stent of embodiment two, wherein the scaffold comprises a crimped state, wherein only α' crystal structure is detectable by WAXD in the crimped state.

The stent of embodiment two, wherein only α' crystal structure is detectable by WAXD in the deployed state.

Embodiment three includes a biodegradable stent comprising: a scaffold including struts comprising a poly(L-lactide)-based biodegradable polymer, wherein the struts have a luminal surface and an abluminal surface, wherein the polymer has induced polymer orientation in the circumferential direction, and wherein the induced orientation decreases from the luminal surface to the abluminal surface of the struts.

The stent of embodiment three, wherein the polymer has the induced orientation in a radial section between the luminal surface and a transition radial distance and no induced orientation between the transition radial distance and the abluminal surface.

The stent of embodiment three, wherein the polymer has the induced orientation in a radial section between the luminal surface and a transition radial distance and no induced orientation between the transition radial distance and the abluminal surface, and wherein the transition radial distance is ⅓ to ½ of the radial thickness of the struts.

The stent of embodiment three, wherein the scaffold is formed by cutting a pattern in a radially expanded tube having the induced orientation that was induced by radially expanding the tube.

The stent of embodiment three, wherein a degree of the induced orientation is uniform around a circumference of the scaffold.

Embodiment four includes a biodegradable stent comprising: a scaffold including struts formed by cutting a pattern of the struts in a tube comprising a poly(L-lactide)-based biodegradable polymer, wherein biodegradable polymer has induced polymer orientation in the circumferential direction of the tube, and wherein the induced orientation decreases from an inner surface to an outer surface of the tube.

The stent of embodiment four, wherein the polymer has the induced orientation in a radial section between the inner surface and a transition radial distance and no induced orientation between the transition radial distance and the outer surface.

The stent of embodiment four, wherein the transition radial distance is ⅓ to ½ of the radial thickness of the tube.

The stent of embodiment four, wherein a degree of the induced orientation is uniform around a circumference of the tube.

The stent of embodiment four, wherein the orientation is induced by radially expanding the tube.

Embodiment five includes a biodegradable stent comprising: a scaffold including struts comprising a poly(L-lactide)-based biodegradable polymer, wherein the struts have a luminal surface and an abluminal surface, and wherein a luminal radial section of the struts exhibits birefringence and an abluminal radial section is optically isotropic when viewed with polarized light.

The stent of embodiment five, wherein the luminal radial thickness is ⅓ to ½ of a radial thickess of the struts from the luminal to abluminal surface.

Embodiment six includes a biodegradable stent comprising: a scaffold including struts formed by cutting a pattern of the struts in a tube comprising a poly(L-lactide)-based biodegradable polymer; and wherein an inner radial section of the tube exhibits birefringence and an outer radial section is optically isotropic when viewed with polarized light.

The stent of embodiment six, wherein the inner radial thickness is ⅓ to ½ of a radial thickess of the tube from the luminal to abluminal surface.

Embodiment seven includes a biodegradable stent comprising: a scaffold including struts made from a tube comprising a poly(L-lactide)-based biodegradable polymer, and wherein the polymer has induced polymer orientation in the circumferential direction and a degree of the induced orientation is uniform around a circumference of the tube.

Embodiment eight includes a biodegradable stent comprising: a scaffold comprising a poly(L-lactide)-based biodegradable polymer in a crimped configuration, wherein the scaffold includes a bending element comprising a first strut section and a second strut section connected at a crest, the bending element flexes inward at the crest when the scaffold is crimped to the crimped configuration, wherein the crest comprises an outer convex sidewall surface and an inner concave sidewall surface, wherein polymer molecular orientation is induced in the crest between the outer convex sidewall surface and the inner concave sidewall surface when the scaffold is crimped and a degree of the induced orientation decreases from the outer convex sidewall surface to the inner concave sidewall surface, wherein the scaffold is radially expandable to a deployed configuration in a blood vessel of a body to hold open the blood vessel.

The stent of embodiment eight, wherein there is no induced orientation in the first strut section and second strut section.

The stent of embodiment eight, wherein there is no change in crystal structure in the crest from a uncrimped configuration to the crimped configuration, the crystal structure being mostly α' morphology.

The stent of embodiment eight, wherein polarized light microscopy of the crests show an increase in retardance from the inner surface and the outer surface.

The stent of embodiment eight, wherein when the scaffold is expanded to the deployed configuration, the induced orientation is retained.

The stent of embodiment eight, wherein when the scaffold is expanded to the deployed configuration, the induced orientation is retained, wherein cracks propagate at the inner surface when the scaffold is deployed with no cracks at the outer surface, the retained orientation inhibiting crack propagation to the outer surface.

The stent of embodiment eight, wherein the crest comprises shear bands at or adjacent to the inner concave sidewall surface.

Embodiment nine includes a biodegradable stent comprising: a scaffold comprising a poly(L-lactide)-based biodegradable polymer having a crimped configuration, wherein the scaffold is radially expandable from the crimped configuration to a deployed configuration, wherein the scaffold includes a bending element comprising a first strut section and a second strut section connected at a crest comprising an outer convex side and an inner concave side, wherein the bending element flexes inward when the scaffold is crimped to the crimped configuration and flexes outward when the scaffold is expanded from the crimped configuration to the deployed configuration, and wherein the inner side is under compression when the scaffold is in the crimped configuration and when the scaffold is deployed, the tension on the inner side is relieved via surface craze regions which grow into diamond-shaped voids that include fibrils spanning the voids upon deployment.

The stent of embodiment nine, wherein the inner side comprises the craze regions in the crimped configuration.

The stent of embodiment nine, wherein the polymer at the inner sidewall surface of the crest has no or lower induced polymer molecular orientation as compared to the outer sidewall surface of the crest.

The stent of embodiment nine, wherein the polymer at the inner sidewall surface of the crest has no or lower induced polymer molecular orientation as compared to the outer sidewall surface of the crest, and wherein the polymer molecular orientation in the outer sidewall surface crest is induced upon crimping and the induced orientation is retained when the scaffold is deployed.

The stent of embodiment nine, wherein the polymer at the inner sidewall surface of the crest has no or lower induced polymer molecular orientation as compared to the outer sidewall surface of the crest, and wherein the outer sidewall surface of the crest comprises no crazing or fracture in the crimped and deployed configurations, the induced polymer orientation at the outer sidewall surface of the crest acts as a barrier to crack propagation from the inner side of the crest.

The stent of embodiment nine, wherein the polymer at the inner sidewall surface of the crest has no or lower induced polymer molecular orientation as compared to the outer sidewall surface of the crest, wherein neither crimping nor deployment induce a change in polymer orientation within the strut sections.

Embodiment ten includes a biodegradable stent comprising: a scaffold comprising a poly(L-lactide)-based biodegradable polymer, wherein the scaffold is radially expandable from a crimped configuration to a deployed configuration, wherein the scaffold includes a bending element comprising a first strut section and a second strut section connected at a crest comprising an outer convex side and an inner concave side, wherein the bending element flexes inward when the scaffold is crimped to the crimped configuration and flexes outward when the scaffold is expanded from the crimped configuration to the deployed configuration, and wherein a degree of induced polymer orientation increases from a strut section and the crest along the outer sidewall surface of the crest.

The stent of embodiment ten, wherein the polymer molecular orientation in the outer crest is induced upon crimping and the induced orientation is retained when the scaffold is deployed.

The stent of embodiment ten, wherein the outer sidewall surface of the crest comprises no crazing or fracture in the crimped and deployed configurations, the induced polymer orientation at the outer sidewall surface acts as a barrier to crack propagation from the inner side of the crest.

The stent of embodiment ten, wherein neither crimping nor deployment induce a change in polymer orientation within the strut sections.

Embodiment eleven includes a biodegradable stent comprising: a scaffold comprising a poly(L-lactide)-based biodegradable polymer, wherein the scaffold is radially expandable from a crimped configuration to a deployed configuration, wherein the scaffold includes a bending element comprising a first strut section and a second strut section connected at a crest comprising an outer convex side and an inner concave side, wherein the bending element flexes inward when the scaffold is crimped to the crimped configuration and flexes outward when the scaffold is expanded from the crimped configuration to the deployed configuration, and wherein polymer molecular orientation is induced in the outer side of the crest upon crimping and the induced polymer orientation is retained when the scaffold is deployed.

The stent of embodiment eleven, wherein the polymer at the inner side of the crests has no or lower induced polymer molecular orientation as compared to the outer side of the crest.

Embodiment twelve includes a biodegradable stent comprising: a scaffold comprising a poly(L-lactide)-based biodegradable polymer, wherein the scaffold is radially expandable from a crimped configuration to a deployed configuration, wherein the scaffold includes a bending element comprising a first strut section and a second strut section connected at a crest comprising an outer convex side and an inner concave side, wherein the bending element flexes inward when the scaffold is crimped to the crimped configuration and flexes outward when the scaffold is expanded from the crimped configuration to the deployed configuration, and wherein the outer sidewall surface of the crest comprises no crazing or fracture in the crimped and deployed configurations, induced polymer orientation at the outer side acts as a barrier to crack propagation from the inner side of the crest.

Embodiment thirteen includes a biodegradable stent comprising: a scaffold comprising a poly(L-lactide)-based biodegradable polymer, wherein the scaffold is radially expandable from the crimped configuration to a deployed configuration, wherein the scaffold includes a bending element comprising a first strut section and a second strut section connected at a crest comprising an outer convex side and an inner concave side, wherein the bending element flexes inward when the scaffold is crimped to the crimped configuration and flexes outward when the scaffold is expanded from the crimped configuration to the deployed configuration, and wherein the retardance of polarized light directed on the bending element increases between the first or second strut section and the crest at the outer side of the crest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 23A-D depict images of samples of an expanded tube, as-cut scaffold, crimped scaffold, and deployed scaffold with an overlay of the initial (tube and as-cut scaffold) azimuthal chain orientation (arrows) and the WAXD reflection orientation of 200/110 crystal (dumbbells).

DETAILED DESCRIPTION OF THE INVENTION

The various embodiments of the present invention relate to polymeric stents and methods of fabricating polymeric stents with favorable mechanical properties. The present invention can be applied to devices including, but is not limited to, self-expandable stents, balloon-expandable stents, stent-grafts, and grafts (e.g., aortic grafts).

Figure 1:
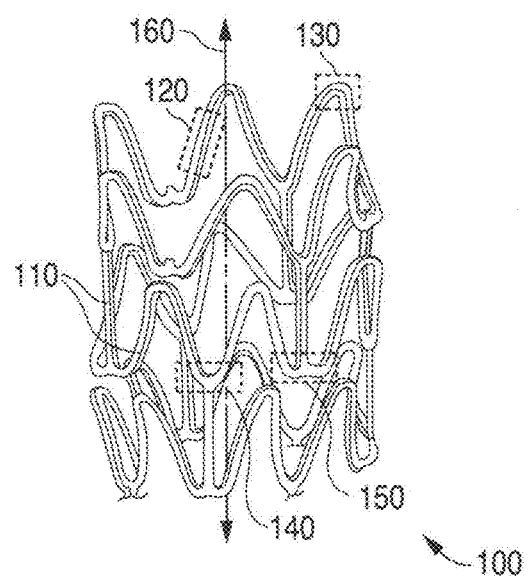
FIG. 1 depicts a stent.

A stent can have a scaffolding or a substrate that includes a pattern of a plurality of interconnecting structural elements or struts. FIG. 1 depicts an example of a view of a stent 100. Stent 100 has a cylindrical shape with an axis 160 and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

The pattern of stent 100 in FIG. 1 varies throughout its structure to allow radial expansion and compression and longitudinal flexure. A pattern may include portions of struts that are straight or relatively straight, an example being a portion 120. In addition, patterns may include bending elements 130, 140, and 150.

Bending elements bend inward when a stent is crimped to allow radial compression. Bending elements also bend outward when a stent is expanded to allow for radial expansion. After deployment, a stent is under static and cyclic compressive loads from the vessel walls. Thus, bending elements are subjected to deformation during use. "Use" includes, but is not limited to, manufacturing, assembling (e.g., crimping stent on a catheter), delivery of stent into and through a bodily lumen to a treatment site, and deployment of stent at a treatment site, and treatment after deployment.

As indicated above, a stent has certain mechanical requirements. A stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Also, a sufficiently low profile, that includes diameter and size of struts, is important. As the profile of a stent decreases, the easier is its delivery, and the smaller the disruption of blood flow.

Polymers tend to have a number of shortcomings for use as materials for stents. One such shortcoming is that many biodegradable polymers have a relatively low modulus, and thus relatively low radial strength. Compared to metals, the strength to weight ratio of polymers is smaller than that of metals. A polymeric stent with inadequete radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under physiological conditions or conditions within a human body. Specifically, such polymers can have a Tg, which is defined below, above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Other potential problems with polymeric stents include creep, stress relaxation, and physical aging. Creep refers to the gradual deformation that occurs in a polymeric construct subjected to an applied load. It is believed that the delayed response of polymer chains to stress during deformation causes creep behavior. Creep occurs even when the applied load is constant. Creep can cause an expanded stent to retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation Physical aging, as used herein, refers to densification in the amorphous regions of a semi-crystalline polymer. Physical aging of semi-crystalline polymers that have glass transition temperatures (Tg) above their normal storage temperature, which, for the purposes of this invention is room temperature, i.e., from about 15° C. to about 35° C., occurs primarily through the phenomenon known as densification. Densification occurs when polymer chains rearrange in order to move from a non-equilibrium state to an equilibrium state. The reordering of polymer chains tends to increase the modulus of the polymer resulting in a brittle or more brittle polymer.

Thus, physical aging results in an increase in brittleness of a polymer which can result in cracking of struts upon crimping and deployment. Since physical aging results from densification of amorphous regions of a polymer, an increase in crystallinity can reduce or inhibit physical aging.

However, it is well known by those skilled in the art that the mechanical properties of a polymer can be modified through various processing techniques, such as, by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus, in the axial and circumferential directions. Therefore, it can be advantageous to modify the mechanical properties of a tube, to be used in the fabrication of a stent, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

Therefore, it can be desirable to fabricate a stent from a polymeric tube with induced orientation in the axial direction and in the circumferential direction. A biaxial oriented tube may be configured to have desired strength and modulus in both the circumferential and axial directions.

The degree of radial expansion, and thus induced radial orientation and strength, of a tube can be quantified by a radial expansion (RE) ratio:

$$\frac{\text{Outside Diameter } (OD) \text{ of Expanded Tube}}{\text{Original Inside Diameter } (ID) \text{ of Tube}}$$

The RE ratio can also be expressed as a percent expansion:

$$\% \text{ Radial expansion} = (\text{RE ratio} - 1) \times 100\%$$

Similarly, the degree of axial extension, and thus induced axial orientation and strength, may be quantified by an axial extension (AE) ratio:

$$\frac{\text{Length of Extended Tube}}{\text{Original Length of Tube}}$$

The AE ratio can also be expressed as a percent expansion:

$$\% \text{ Axial expansion} = (\text{AE ratio} - 1) \times 100\%$$

In some embodiments, a polymeric tube may be deformed by blow molding. In blow molding, a tube can be deformed or expanded radially by increasing a pressure in the tube by conveying a fluid into the tube. The polymer tube may be deformed or extended axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a cylindrical member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold.

The temperature of the tube can be heated to temperatures above the Tg of the polymer during deformation to facilitate deformation. The polymer tube may also be heated prior to, during, and subsequent to the deformation. In one embodiment, the tube may be heated by conveying a gas above ambient temperature on and/or into the tube. The gas may be the same gas used to increase the pressure in the tube. In another embodiment, the tube may be heated by translating a heating element or nozzle adjacent to the tube. In other embodiments, the tube may be heated by the mold. The mold may be heated, for example, by heating elements on, in, and/or adjacent to the mold.

Certain embodiments may include first sealing, blocking, or closing a polymer tube at a distal end. The end may be open in subsequent manufacturing steps. The fluid, (conventionally a gas such as air, nitrogen, oxygen, argon, etc.) may then be conveyed into a proximal end of the polymer tube to increase the pressure in the tube. The pressure of the fluid in the tube may act to radially expand the tube.

Additionally, the pressure inside the tube, the tension along the cylindrical axis of the tube, and the temperature of the tube may be maintained above ambient levels for a period of time to allow the polymer tube to be heat set. Heat setting may include maintaining a tube at a temperature greater than or equal to the Tg of the polymer and less than the Tm of the polymer for a selected period to time. The selected period of time may be between about one minute and about two hours, or more narrowly, between about two minutes and about ten minutes.

In heat setting, the polymer tube may then be cooled to below its Tg either before or after decreasing the pressure and/or decreasing tension. Cooling the tube helps insure that the tube maintains the proper shape, size, and length following its formation. Upon cooling, the deformed tube retains the length and shape imposed by an inner surface of the mold.

Properties of a polymer such as fracture toughness are affected by the overall degree of crystallinity and the number and size of crystal domains in a semi-crystalline polymer. It has been observed that fracture toughness is increased by having a large number of small crystal domains in a polymer surrounded by an amorphous domain. Such a crystal structure can also reduce or prevent creep, stress relaxation, and physical aging. In some embodiments, the size of crystal domains may be less than 10 microns, 4 microns, or, more narrowly, less than 2 microns. The overall crystallinity may be less than 50%, 40% or, more narrowly, less than 20%.

In certain embodiments, the temperature of the deformation process and/or heat setting can be used to control the crystallinity to obtain the desired crystal structure described above. In general, crystallization tends to occur in a polymer at temperatures between Tg and Tm of the polymer and it varies with temperature in this range. In some embodiments, the temperature can be in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, 50, 100, or greater than 100. In another embodiment, the temperature range may be in range between about Tg to about 0.2(Tm−Tg)+Tg.

Figure 2A:
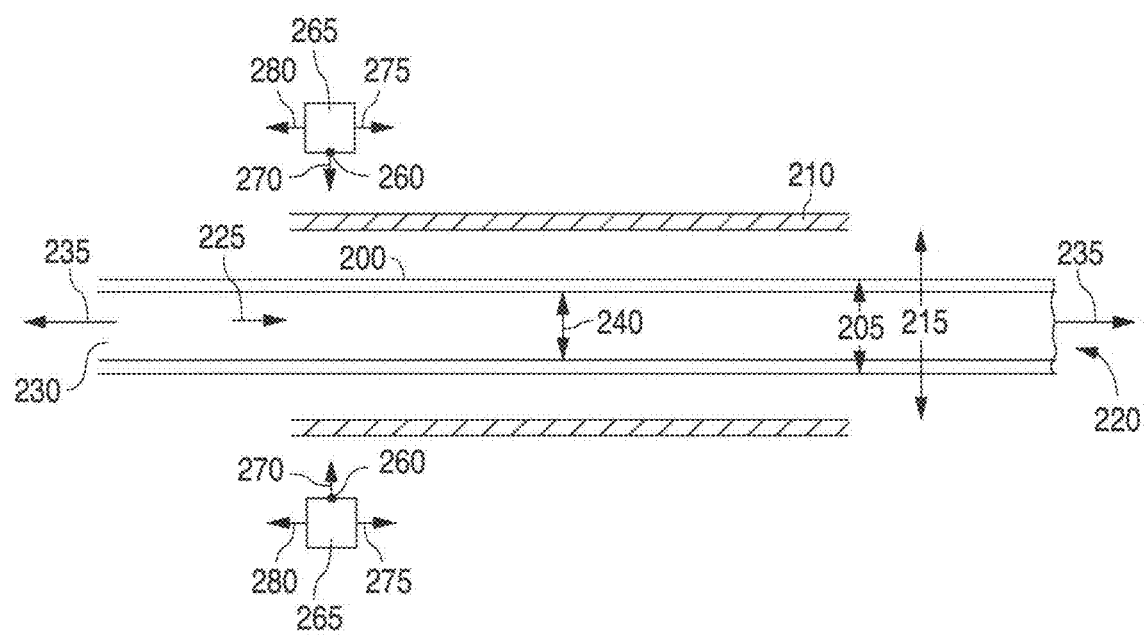
FIGS. 2A-C depict blow-molding of a polymeric tube.
Figure 2B:
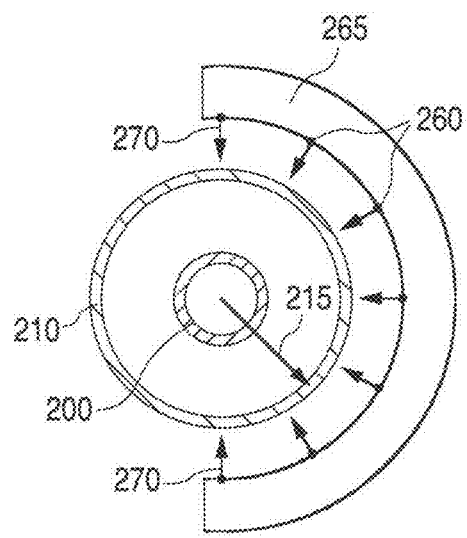
Figure 2C:
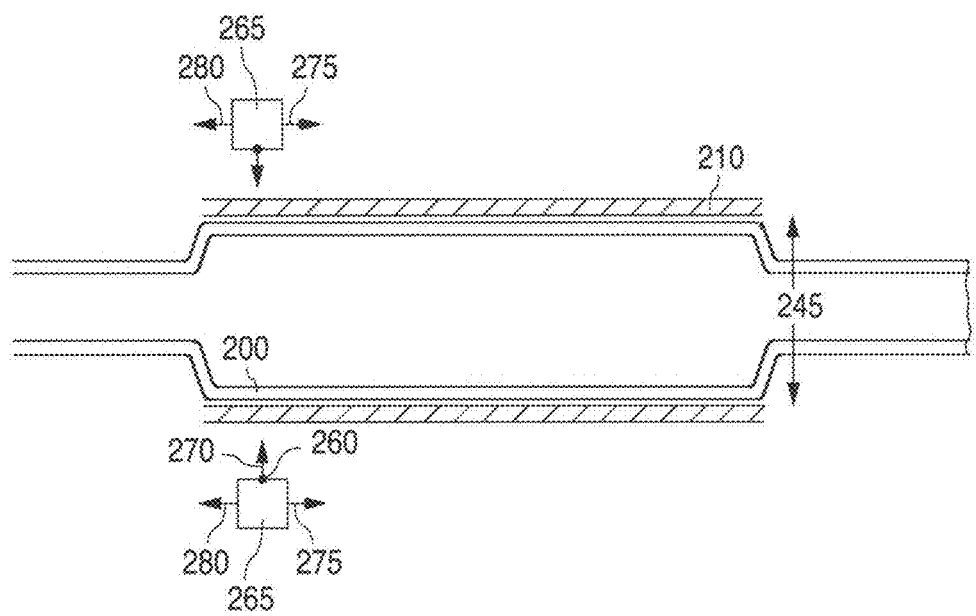

FIGS. 2A-C illustrate an embodiment of blow molding a polymer tube for use in manufacturing a stent. FIG. 2A depicts an axial cross-section of a polymer tube 200 with an outside diameter 205 positioned within a mold 210. FIG. 2B depicts a radial cross-section of polymer tube 200 and mold 210. Mold 210 may act to limit the radial deformation of polymer tube 200 to a diameter 215, the inside diameter of mold 205. Polymer tube 200 may be closed at a distal end 220. Distal end 220 may be open in subsequent manufacturing steps. A fluid may be conveyed, as indicated by an arrow 225, into an open proximal end 230 of polymer tube 200. A tensile force 235 is applied at proximal end 230 and a distal end 220.

Polymer tube 200 is heated by heating nozzles 260 on a support 265 that blow a heated gas as shown by arrows 270. Support 265 translates back and forth along the axis of the mold as shown by arrows 275 and 280. The increase in pressure inside of polymer tube 200, facilitated by an increase in temperature of the polymer tube, causes radial deformation of polymer tube 200, as indicated by an arrow 240. FIG. 2C depicts polymer tube 200 in a deformed state with an outside diameter 245 within mold 210.

Figure 3:
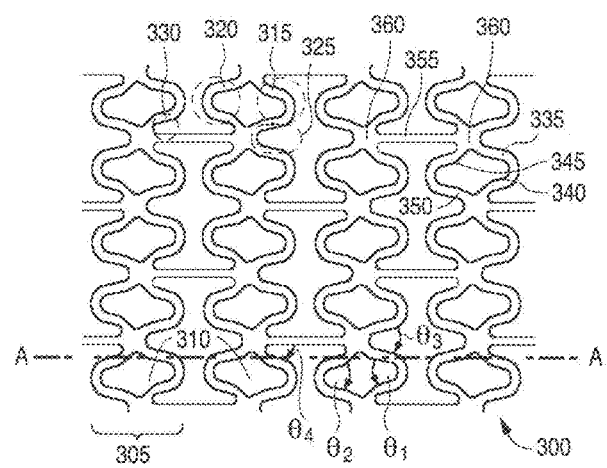
FIG. 3 depicts an exemplary stent pattern.

To illustrate the importance of orientation in a stent pattern, FIG. 3 depicts an exemplary stent pattern 300 for use with embodiments of a polymeric tube or a sheet. In an embodiment, stent pattern 300 can be cut from a polymeric tube using laser machining. Stent pattern 300 is shown in a flattened condition so that the pattern can be clearly viewed. When the flattened portion of stent pattern 300 is in a cylindrical form, it forms a radially expandable stent.

As depicted in FIG. 3, stent pattern 300 includes a plurality of cylindrical rings 305 with each ring including a plurality of diamond shaped cells 310. Embodiments of stent pattern 300 may have any number of rings 305 depending on a desired length of a stent. For reference, line A-A represents the longitudinal axis of a stent using the pattern depicted in FIG. 3. Diamond shaped cells 310 include bending elements 315 and 320. Stent pattern 300 can also includes bending elements 325 and 330. The angles of bending elements 315, 320, 325, and 330 correspond to angles $\theta_1$, $\theta_2$, $\theta_3$, and $\theta_4$. Angles $\theta_1$, $\theta_2$, $\theta_3$, and $\theta_4$ are 42, 42, 41, and 21 degrees, respectively. Diamond shaped cells 310 are made up of bar arms 335 and 340 that form bending element 315 and bar arms 345 and 350 that form bending element 320.

When stent 300 is crimped, bending elements 315, 320, 325, and 330 flex inward and angles $\theta_1$, $\theta_2$, $\theta_3$, and $\theta_4$ decrease, allowing the stent to be radially compressed. With respect to bending elements 315, 320, and 325, struts on either side of the bending elements bend toward each other. However, in bending element 330, the strut of the diamond-shaped element tends to bend toward the linking strut which tends to remain relatively parallel to the longitudinal axis during crimping.

Pattern 300 further includes linking arms 355 that connect adjacent cylindrical rings. Linking arms 355 are parallel to line A-A and connect adjacent rings between intersection 360 of cylindrically adjacent diamond-shaped elements 310 of one ring and intersection 360 of cylindrically adjacent diamond shaped elements 310 of an adjacent ring. As shown, linking elements connect every other intersection along the circumference.

Figure 4:
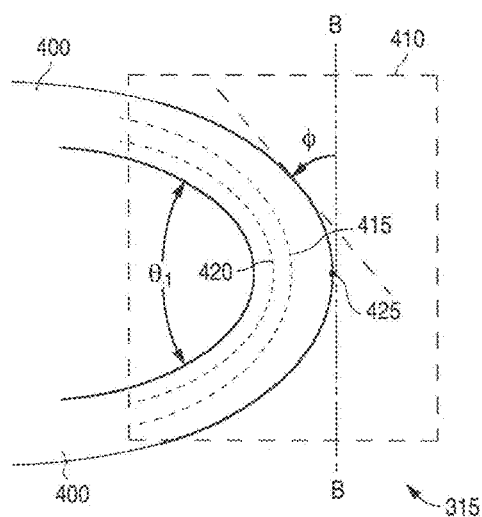
FIG. 4 depicts a bending element from the pattern in FIG. 3.

The curved portions of bending elements experience substantial stress and strain when a stent is crimped and deployed. Therefore high strength and toughness are very important in these regions. For example, a close-up view of bending element 315 is depicted in FIG. 4 to illustrate the direction of stress in a bending element. Compressive and outward radial stress on a stent cause substantially no strain in straight sections 400. However, such radial stresses result in relatively high stress and strain in curved portion 410 of bending element 315. For example, when a stent is expanded, angle $\theta_1$ of bending element 315 increases. The region above a neutral axis 415 experiences relatively high compressive stress and strain and the region below neutral axis 415 experiences relatively high tensile stress and strain. Alternatively, when a stent is crimped, angle $\theta_1$ of bending element 315 decreases and there is tensile stress and strain above neutral axis 415 and compressive stress and strain below neutral axis 415.

The tensile and compressive strain follow the axis or curvature of bending element 315, for example, line 420. Ideally, the most effective orientation to improve fracture toughness is along the length of the axis of the strut. However, radial expansion imparts orientation and fracture toughness along the circumferential direction, as shown by line B-B. An angle φ between a point on the axis of the stent and the circumferential direction B-B tends to decrease moving along bending element 315 from the straight sections 400 to an apex 425 of bending element 315.

An exemplary stent having the pattern of FIG. 3 can be cut from a poly(L-lactide) (PLLA) tube that is about 0.084 in inside diameter. A desired crimped diameter may be about 0.055 in and an expanded diameter about of 0.134 in. Such a stent can be fabricated from an extruded tube that is radially expanded between 200% and 400%. For a stent with the pattern shown in FIG. 3, and the dimensions provided above, cracks have been observed to form in the curved portion of bending elements upon expansion of the stent to the expanded diameter.

For a given radius of curvature, increasing angle $\theta_1$ of bending element 315 tends to increase angle φ along the axis of bending element 315, making bending element 315 along curved portion 410 closer in orientation with the circumferential direction B-B. As a result, the strength and toughness of bending element 315 are increased when there is induced radial orientation in the stent. The relative orientation of points along the axis, angle φ, of a bending element also depends on the radius of curvature. Increasing the radius of curvature of bending element 315 also makes bending element 315 along curved portion 410 closer in orientation with the circumferential direction B-B.

Therefore, it is advantageous to decrease the relative orientation between the axis of bar arms or struts in curved portions and the circumferential direction in a fabricated stent. Certain embodiments of the invention include stents having bending elements with angles greater than about 80°, or more narrowly, greater than about 90°, or 110°. The stent may have an uncrimped or fabricated diameter that allows the stent to be crimped to a selected crimped diameter at which the bending elements have an angle between 0° to 50°, or more narrowly between 0° to 30°.

Figure 5:
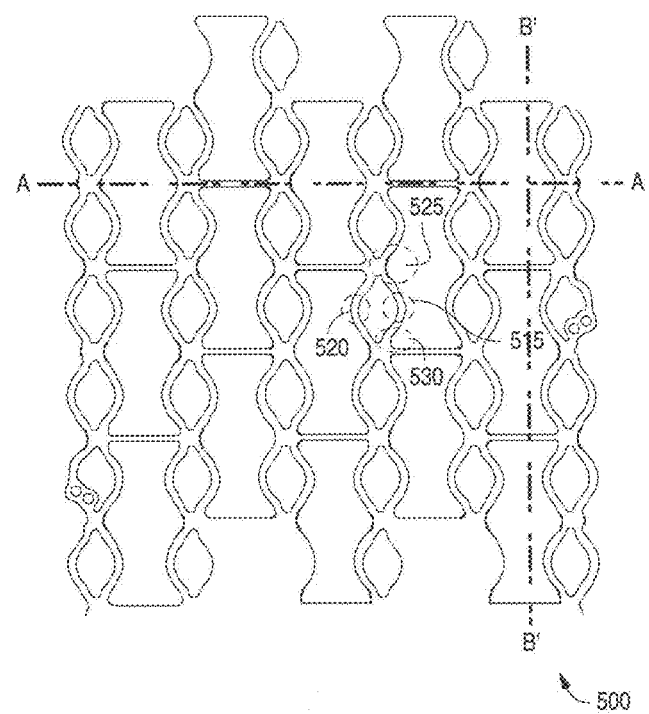
FIG. 5 depicts an alternative stent pattern.

FIG. 5 depicts a stent pattern 500 similar to pattern 300 in FIG. 3. The angles of bending elements 515, 520, 525, and 530 are about 113°, 113°, 116°, and 55°, respectively. Therefore, the orientation of points on the axis of the bending elements of pattern 500 are closer to the circumferential direction than that in stent pattern 300. The radii of curvature of bending element 515 and 520 can be between about 0.014 in and 0.02 in. The radii of curvature of bending element 525 can be between about 0.009 in and 0.013 in. The radii of curvature of bending element 525 can be between about 0.0026 in and 0.0035 in.

In an embodiment, the outside diameter (OD) of a fabricated stent can be between 0.07 in and 0.165 in. The crimped diameter of a stent having stent pattern 500 may be less than 0.06 in, 0.036 in, 0.032 in, or more narrowly less than 0.028 in.

In certain embodiments, it may be advantages to fabricate a stent from a tube that has been radial expanded to greater than 400%. As indicated above, cracks have been observed in high strain regions of stent fabricated from a tube expanded in the 200% to 400% range. In some embodiments, a stent may be fabricated from a tube that has been radial expanded to greater than 500%, 600%, 700%, or greater than 800%. The tube may be used to fabricate stents having a variety of patterns. In some embodiments, a stent with a stent pattern 500 can be fabricated from tube radially expanded to greater than 400%.

Such a stent may then show a greater increase in fracture toughness and stress over a stent fabricated from a tube radially expanded in a range between 200% and 400%. As a result, such a stent may have fewer or no cracks when expanded to an intended deployment diameter. Increasing the degree of expansion tends to impart greater strength and toughness. Thus, increasing the degree of expansion may extend the range of a diameter that a stent can be deployed.

Exemplary process conditions for expanding a PLLA tube between 400% and 700% include a temperature of heated air at the heat nozzle between 205° F. and 285° F. The heat nozzle air flow rate can be between about 60 and 65 SCFH (standard cubic feet per hour). The pressure of nitrogen conveyed into the tube can be between 177 psi and 250 psi. The tension applied axially to extend the tube can be between about 75 g and 105 g.

The advantages of expanding in a range greater than 400% is shown by the following example. A PLLA tube was extruded to an ID of 0.024 in and an OD of 0.074 in. The extruded tubing was radially expanded using blow molding 470% to an ID of 0.125 in and OD of 0.137 in. Five stents were prepared from the expanded tubing. The expanded tubing was laser cut to form a stents with a pattern similar to stent pattern 500 in FIG. 5. The stents were crimped, mounted on a catheter, and sterilized with E-beam radiation.

Figure 6:
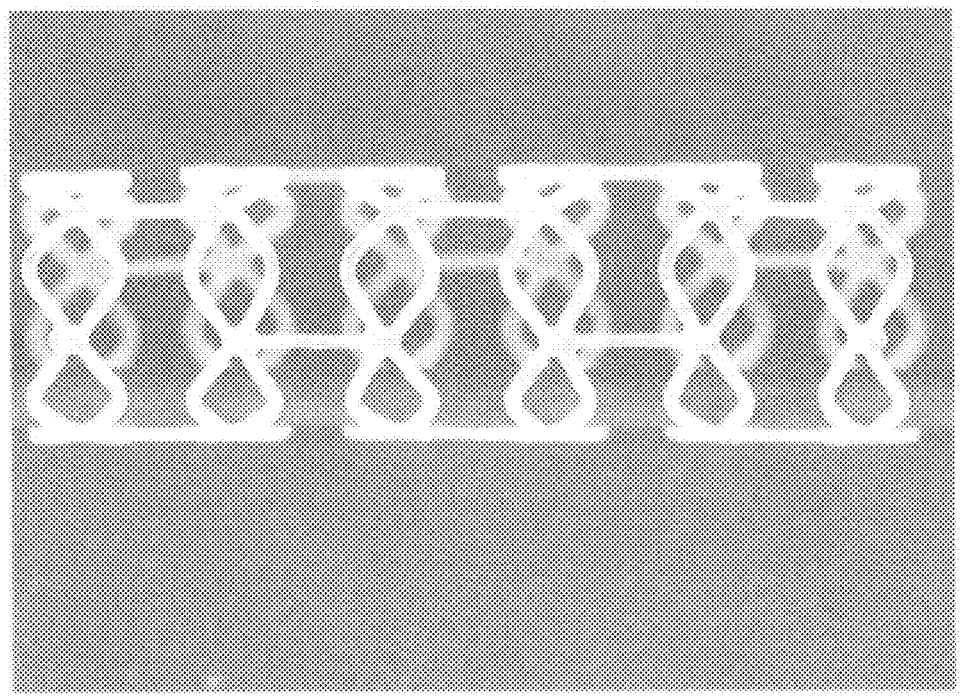
FIGS. 6-8 depict images of expanded stents.
Figure 7:
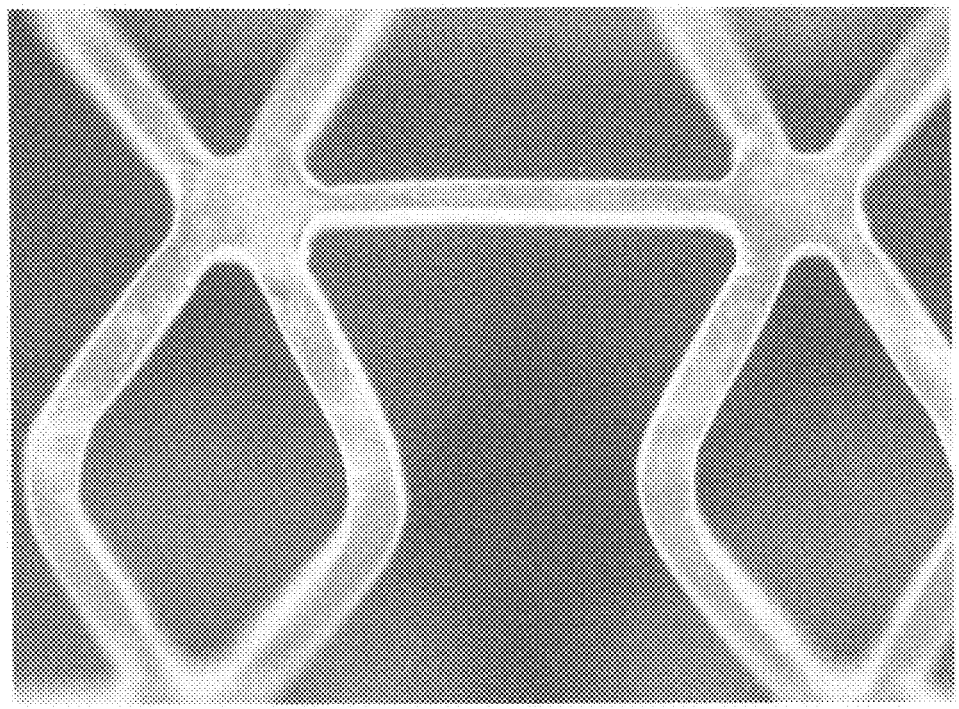

The stents were expanded by a balloon on the catheter in a 37° C. water bath to 0.138 in. The stents were removed and examined. FIGS. 6 and 7 show images of a stent expanded to 0.138 in. FIG. 6 depicts the entire stent and FIG. 7 depicts a close-up view. The stent appears to be substantially free of cracks.

Figure 8:
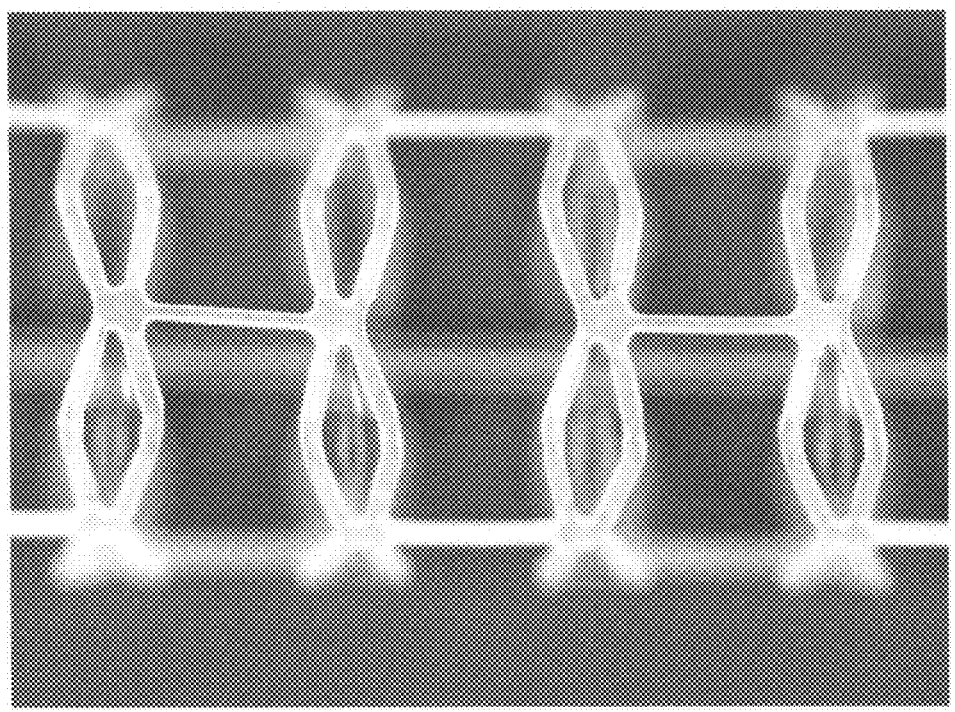

The stents were placed on another catheter and expanded further to 0.158 in. FIG. 8 depicts an image of this expanded stent which shows cracks forming in the high strain regions. The images demonstrate the effectiveness of increased biaxial orientation for the PLLA system.

As shown above, radial expansion above 400% can increases fracture toughness of an expanded stent. Radial expansion above 400% can also address other issues with polymeric stents, such as stent retention during crimping and physical aging during long term storage.

As discussed above, physical aging results in an increase in brittleness of a polymer which can result in cracking of struts upon crimping and deployment. Polymeric stents generally are stored below ambient temperatures to reduce or prevent physical aging the polymer that can cause cracking in stent struts during crimping and deployment. Stents can be stored in freezers at temperatures below 0° C. Storing the polymeric stents at low temperature reduces the segmental motions of polymer chains that result in densification.

In general, it would be desirable to store a polymeric stent close to ambient temperature. However, many polymers have Tg's low enough to allow significant long term aging or densification to occur during the time frame of long term storage, which can be a few days, a month, 3 months, 6 months, or more than 6 months. Although Tg is defined as the temperature at which the onset of segmental motion in the chains of the polymer occurs, the glass transition is not sharp or discontinuous for a polymer with amorphous regions. Rather, there is a gradual transition from the brittle to the ductile state corresponding to a gradual increase in segmental motion. Thus, even for polymers with Tg's above ambient temperatures, significant physical aging can occur during long term storage. Increasing the difference between the storage temperature and the Tg reduces the segmental motion of polymer chains which reduces or eliminate the effects of long term aging.

In addition, crimping of a polymeric stent at ambient temperatures can result in an outward recoil of the stent from the crimped radius, reducing stent retention on the catheter. Due to shape memory of the polymer, the stent recoils outward toward the fabricated diameter.

Such outward recoil can be reduced by heating the stent above ambient temperatures during crimping. However, it has been observed that elevated crimping temperatures can result in fracture of struts during crimping and upon deployment. Specifically, a PLLA stent fabricated from a polymeric tube expanded 300% from an extruded tube that is crimped at 50° C. results in fracture during deployment. This observed increase in mechanical damage to the stent is a result of stress relaxation of the polymer during the crimping process, due to the crimping being conducted close to the Tg of the polymer. This stress relaxation will result in greater experienced stress during the expansion of the stent during deployment. This will, in turn, result in a greater probability of cracking during the expansion of the stent.

Increasing the difference between the elevated crimping temperature and the Tg reduces the likelihood of cracking of struts.

In general, deforming a polymer form or construct can increase the Tg of the polymer. The increased order from orientation and induced crystallization caused by deformation tends to increase the temperature necessary for segmental motion of polymer chains, which corresponds to Tg.

For a given polymer system, the degree of deformation, or specifically, expansion of a polymeric tube, may be correlated with an increase in Tg. Thus, an increase in Tg can allow storage of the polymer form at a higher temperature with little or no negative effects of physical aging, or other visco-elastic phenomena. For example, the Tg can be increased to allow storage at ambient temperature. In addition, the Tg can be increased to allow crimping at a selected elevated temperature without cracking of stent struts.

In certain embodiments, a stent can be fabricated from a polymeric tube that allows crimping at a selected elevated temperature with no or substantially no cracking of struts. The polymeric tube can be radially expanded to a degree of expansion that allows crimping at the elevated temperature. The degree of expansion can be between 200% and 400%. In other embodiments, the degree of expansion can be between 400% and 800%. The selected elevated temperature can be at least 10° C., 20° C., 30° C., 40° C., or 50° C. below the Tg of the polymer.

In additional embodiments, a stent can be fabricated from a polymeric tube that allows long term storage at a selected temperature. For example, the temperature can be at or near an ambient temperature. The polymeric tube can be radially expanded to a degree of expansion that allows storage at the selected temperature with little or no negative effects of physical aging. As above, the degree of expansion can be between 200% and 400%. In other embodiments, the degree of expansion can be between 400% and 800%. The storage temperature can at least 30° C., 40° C., 50° C., 60° C., or 70° C. below the Tg of the polymer.

Differential scanning calorimetry (DSC) was used to study the increase in the Tg due the radial orientation induced by radial expansion. In general, DSC is a technique that may be used to identify thermal transitions in a polymer. Thermal transitions include, for example, crystallization and melting. A thermal transition in a polymer may be endothermic (sample absorbs heat) or exothermic (sample expels heat). Glass and melting transitions are exothermic and crystallization is endothermic.

In a typical DSC run, a polymer sample is heated at a constant rate. The heat inflow or outflow into the sample is controlled to keep the heating rate constant. When the sample undergoes a thermal transition, heat is either absorbed or expelled. At the glass transition and melting transition, heat flow into the sample decreases. When a polymer sample crystallizes, the heat flow into the sample increases.

The Tg of PLLA tubes was studied at 300% and 500% radial expansion. DSC runs were performed for two samples for each degree of expansion. For 500% radial expansion PLLA tubing was extruded to an ID of 0.021 in and an OD of 0.072 in. For 300% radial expansion, PLLA tubing was extruded to an ID of 0.018 in and an OD of 0.056 in. The extruded tubing was radially expanded using blow molding.

Figure 9:
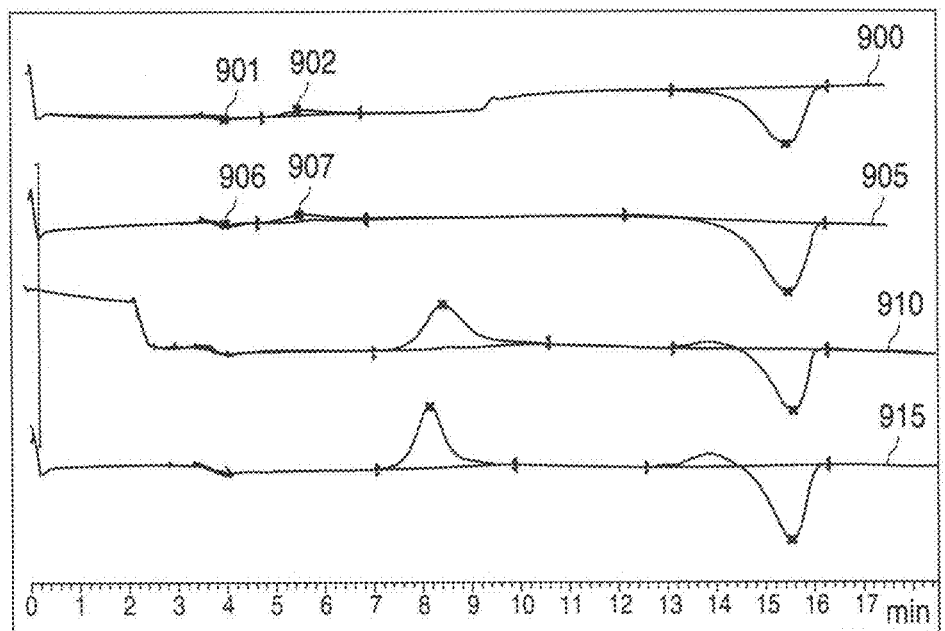
FIGS. 9-10 depict graphs of differential scanning calorimetry results.

FIG. 9 depicts the results of DSC runs for samples expanded to 300%. Curve 900 corresponds to the first sample and curve 905 corresponds to the second sample. Troughs 901 and 906 depict the glass transition, which is about 62° C. in each case. In addition, peaks 902 and 907 correspond to the crystallization transition of the polymer for the first and second samples, respectively.

The melted samples at the end of each run were quenched to a solid form. DSC runs were then performed on the quenched samples for comparison. These samples correspond to PLLA without induced orientation. Curve 910 corresponds to the first sample and curve 915 corresponds to the second sample.

Figure 10:
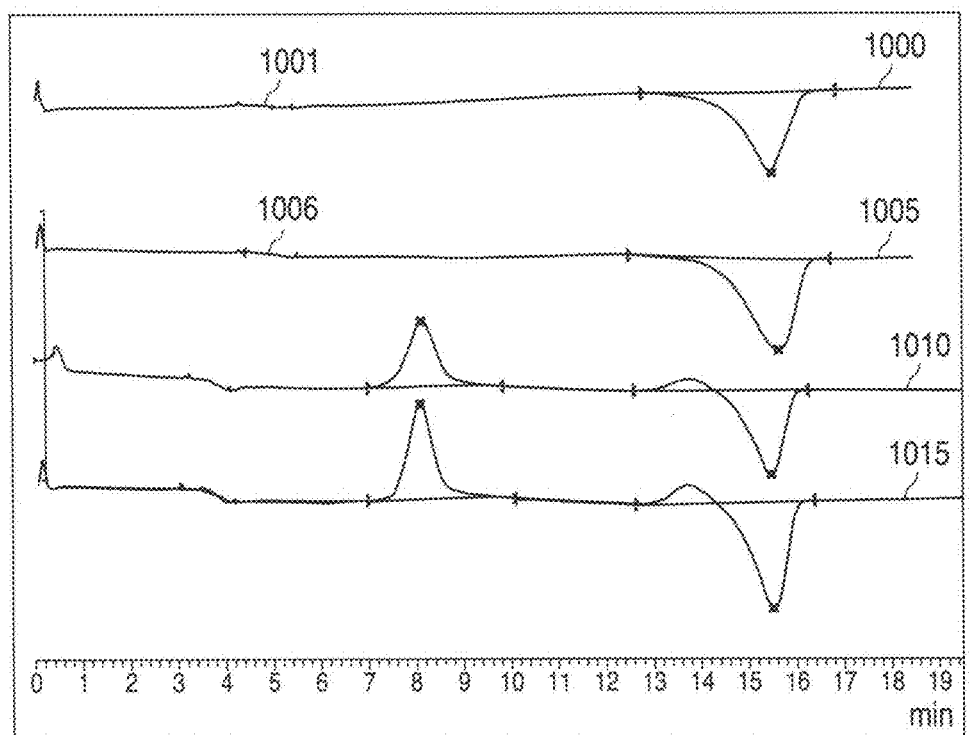

FIG. 10 depicts the results of DSC runs for samples expanded to 500%. Curve 1000 corresponds to the first sample and curve 1005 corresponds to the second sample. Troughs 1001 and 1006 depict the glass transition, which is about 71° C. in each case. Curves 1000 and 1005 do not have peaks analogous to peaks 902 and 907 in FIG. 9. This indicates that polymer of the samples expanded 500% was completely or almost completely crystallized due to stress induced crystallization. The high crystallinity reduces physical aging. The melted samples at the end of each run were quenched to a solid form. DSC runs were then performed on the quenched samples for comparison. These samples correspond to PLLA without induced orientation. Curve 1010 corresponds to the first sample and curve 1015 corresponds to the second sample.

Thus, the Tg increased from 62° C. to 71° C. from 300% to 500% radial expansion. A stent fabricated from a tube expanded 500% was crimped at 50° C. without strut fracture. Also, it is expected that the increase in Tg allows for an increase in storage temperature.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

The manufacturing process of a bioabsorbable polymer stent or scaffold includes making a polymer tube from a polymer resin, processing to increase strength, laser cutting the tube to form a stent pattern in the expanded tube, crimping the scaffold over a catheter, packaging, sterilization (e.g., e-beam exposure). The processing to increase strength includes heating the polymer tube between Tg and Tm or tube expansion between Tg and Tm. The process can further include placement of radiopaque markers in or on the scaffold after laser cutting and before crimping. Additionally, a coating of a polymer and drug may be formed over the scaffold after laser cutting.

The microstructure or morphology of the polymer changes as it proceeds through the manufacturing process. Specifically, the microstructure changes when the tube is heated and radially expanded and when the scaffold is crimped. Additionally, the microstructure changes when the scaffold is deployed or expanded from a crimped configuration. As discussed herein, the microstructure includes the degree of crystallinity of the polymer, polymer crystallite and polymer chain orientation in the circumferential direction, and the degree of orientation. The microstructure further includes the type of crystalline forms and the relative amount of crystalline forms.

Crystallization of polymers is a process associated with partial alignment of their molecular chains. These chains fold together and form ordered regions called lamellae, which in turn assemble into larger structures. Orientation of lamellae results in birefringence producing a variety of colored patterns when specimens are viewed between crossed polarizers in an optical microscope. Orientation can refer to orientation of polymer chains within lamellae, orientation of a crystal lamella or a larger assembly of lamellae, or orientation of polymer chains in an amorphous region. The orientation of one or any of these can be random (isotropic) or can be preferentially oriented (anisotropic).

Figure 11:
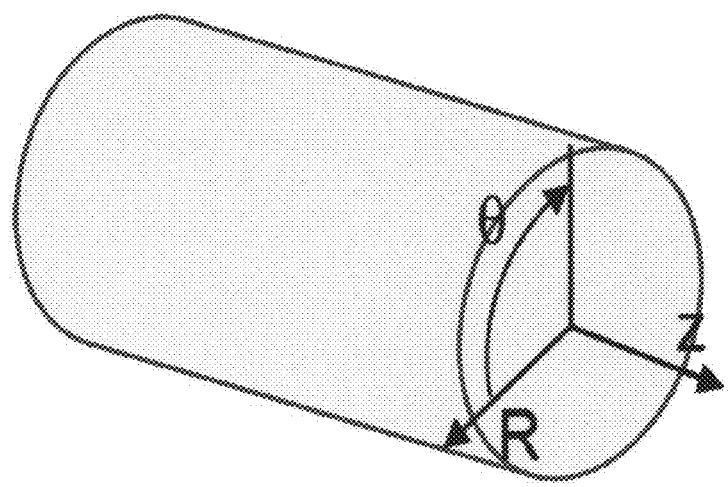
FIG. 11 depicts a tube illustrating the cylindrical coordinate system for a tube or scaffold geometry useful for characterizing spatial variation in microstructure properties.

FIG. 11 depicts a tube illustrating the cylindrical coordinate system for a tube or scaffold geometry useful for characterizing spatial variation in microstructure properties. R refers to the radial direction, $\theta$ refers to the azimuthal (or circumferential) direction, and Z is the longitudinal or axial direction. Polymer crystal orientation of a tube or a scaffold can be characterized as being in the azimuthal or axial directions. As described herein, radial expansion of a polymer tube including a polymer such as PLLA initially results in higher crystallinity and preferred orientation in the azimuthal direction.

During polymer stretching, such as in stretch-blow molding, semi-crystalline polymeric materials can be shaped at temperatures between Tg and Tm. Crystallization and orientation of polymers that occurs during stretching is correlated to the relaxation time of the chains. Reptation refers to the thermal motion of polymer chains in an entangled state. When the draw ratio rate is slower than the rate of polymer chain reptation, no oriented crystallization is observed. At high strain rates, chain deformation is faster than the rate of chain relaxation, which promotes chain orientation. When the chain orientation reaches the critical value that accelerates crystal nucleation, crystallization occurs and proceeds faster than the chain relaxation can occur.

Cavitation that can occur during deformation can alter the structure transformation of crystals. With increasing deformation, cavities change in size, number and orientation. It has been shown that stretching PLLA initially results in higher crystallinity and preferred orientation. However, at high strain rates voids and cavities appear and grow [Zhang et al. Polymer 52 (2011) 4141-4149].

Depending on processing conditions (temperature and strain), PLLA exists in four different crystalline forms: $\alpha$, $\alpha'$, $\beta$ and $\gamma$. It has been shown that $\alpha'$ can transform to the $\alpha$ phase through an irreversible process because $\alpha$ is a more stable phase [Kalish et al. Polymer 52 (2011) 814-821]. The formation of $\alpha$ and $\alpha'$ crystal structures in PLLA have been described in Zhang et al. Macromol. Symp. 242 (2006) 274-278 and Stoclet et al. 43 Macromolecules (2010) 1488-1498. Little is known about the effect of strain and temperature on microstructure, particularly below Tg, as in the crimping and deployment of a PLLA-based scaffold, on the transformation from $\alpha'$ to $\alpha$.

The change in the polymer microstructure was studied for the expanded tube, as-cut scaffold, crimped scaffold, and deployed scaffold. The samples studied were made of PLLA. The degree of crystallinity and crystalline microstructure of the polymer depend on the thermal and deformation history during processing. In turn, the semicrystalline morphology determines strength and biodegradation. Techniques were used to provide spatially-resolved information about the resulting polymer microstructure. The techniques used to characterize the polymer were polarized light microscopy (PLM), wide angle X-ray scattering (WAXD), and combined small angle X-ray scattering (SAXS) and WAXD.

Polarized Light Microscopy was used to determine distribution of crystallite orientation within an expanded tube and the scaffold wall. Polarized light microscopy refers to optical microscopy techniques involving illumination of sample with polarized light. These illumination techniques are most commonly used on birefringent samples where the polarized light interacts strongly with the sample and so generates contrast with the background.

Birefringence refers to the optical property of a material having a refractive index that depends on the polarization and propagation direction of light. These optically anisotropic materials are said to be birefringent (or birefractive). The birefringence is often quantified as the maximum difference between refractive indices exhibited by the material. Crystals with asymmetric crystal structures are often birefringent as well as plastics under mechanical stress. Optical isotropy means having the same optical properties in all directions. This can mean, e.g., that the crystallites are smaller than the resolution limit, or that the crystallites are randomly oriented relative to each other and therefore have no measurable difference in orientation.

Figure 12:
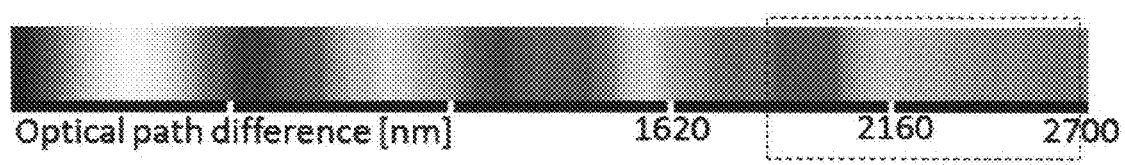
FIG. 12 depicts the Michel-Levy chart that includes interference colors that describe optical retardance due to crystallite orientation.

Polarized light microscopy is capable of distinguishing between isotropic and anisotropic substances. There are two polarizing filters in a polarizing microscope termed the polarizer and analyzer. The Michel-Levy Chart arises when polarized white light is passed through a birefringent sample. FIG. 12 depicts the Michel-Levy chart that includes interference colors that describe optical retardance due to crystallite orientation.

Retardance refers to the difference in phase shift between two characteristic polarizations of light upon reflection from an interface. The silver at the far left indicates very little orientation and the sequence of colors from right to left reveals increasing orientation. The variation in the sequence from left to right may also indicate variation in crystallinity.

PLM micrographs were acquired by placing sections of the tube or scaffold between crossed polars of a Carl Zeiss microscope. The birefringence variation across the sections is due to the combination of preferentially oriented amorphous and oriented crystalline material.

Synchrotron X-ray scattering provides information about crystalline morphology with high spatial resolution. It can provide information about the amount of crystallinity, crystal morph, and the crystal orientation at very small length scales. Small-angle X-ray scattering (SAXS) reveals information about structure in the nanoscale whereas wide-angle scattering or diffraction (WAXS or WAXD) gives us information in the unit cell (angstrom) scale.

WAXD was used to determine crystal structures, quantify degree of crystallinity, and characterize the orientation distribution of crystallites. Beam spot size varies depending on synchrotron source; spot size enables measurements of different spatial resolution: (1)Advanced Light Source (ALS), Lawrence Berkeley Lab: 200 µg×100 µm; (2) Advanced Photon Source (APS); (3) Argonne National Lab: 0.2 µg; and (4) Brookhaven National Lab: 380 µg, 20 µg.

SAXS was used to characterize nanoscale arrangement of crystallites. SAXS can be used in combination with WAXD to map crystalline behavior at multiple length scales simultaneously. Simultaneous SAXS/WAXS scattering experiments were performed at the National Synchrotron Light Source at Brookhaven National Lab (B). SAXS experiments used a Mar 165 CCD and WAXS used a custom Photonics detector that captured a quadrant of the scattering patterns. The source wavelength, $\lambda$, was 0.92 Å and the beam spot size was 20 µg. The simultaneous SAXS and WAXS data provide information about crystallinity and nano-scale arrangement at a specific position.

The tube and scaffold samples in the microstructure studies were made from a PLLA resin obtained from Evonik. The tube samples for the scaffolds are formed by extrusion. In the radial expansion, tubes were heated above the Tg of the polymer. The temperature range of the heating is 75-120° C., with an infra-red lamp and is expanded with pressurized air within a glass mold. Percent radial expansion (((IDexp/ID original)−1)×100%) was 400% and percent axial elongation ((Lexp/Loriginal)−1)×100%) was 20 to 25%. The expanded tubes were laser cut to form the scaffold samples. The fabricated or uncrimped outer diameter (OD) of the scaffold samples was 3.5 mm.

Figure 13A:
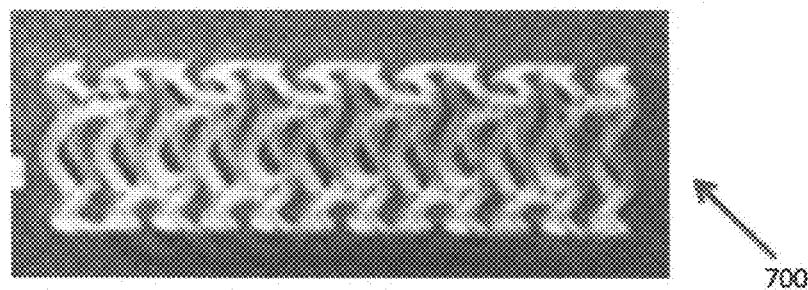
FIGS. 13A-D depict images of the sample scaffolds.
Figure 13B:
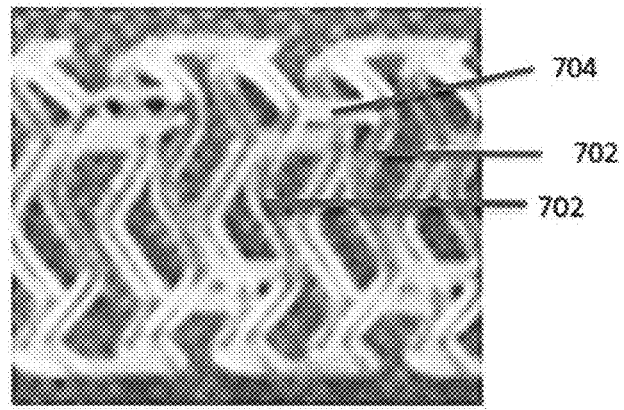
Figure 13C:
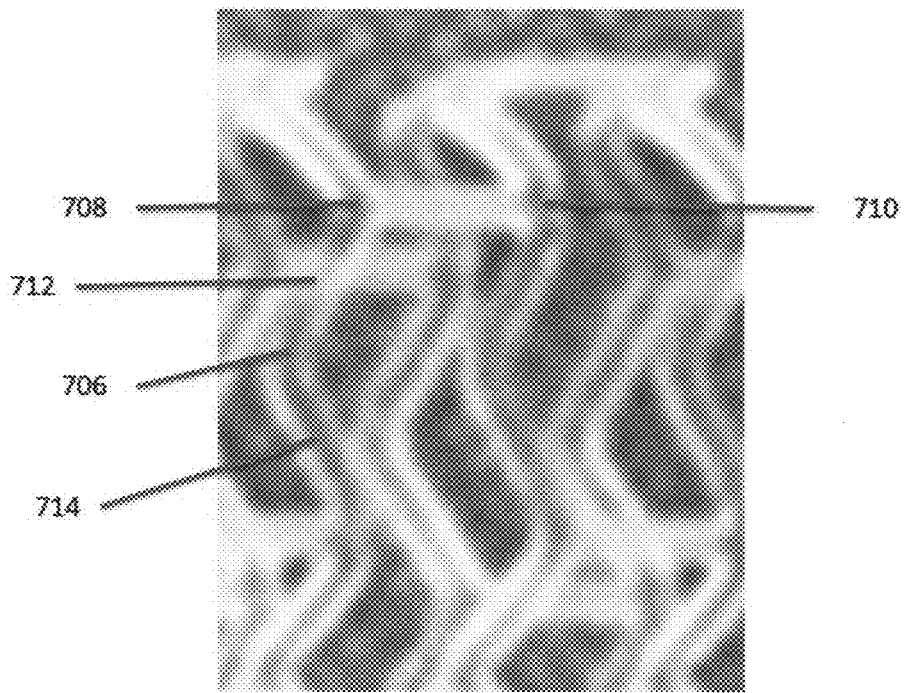
Figure 13D:
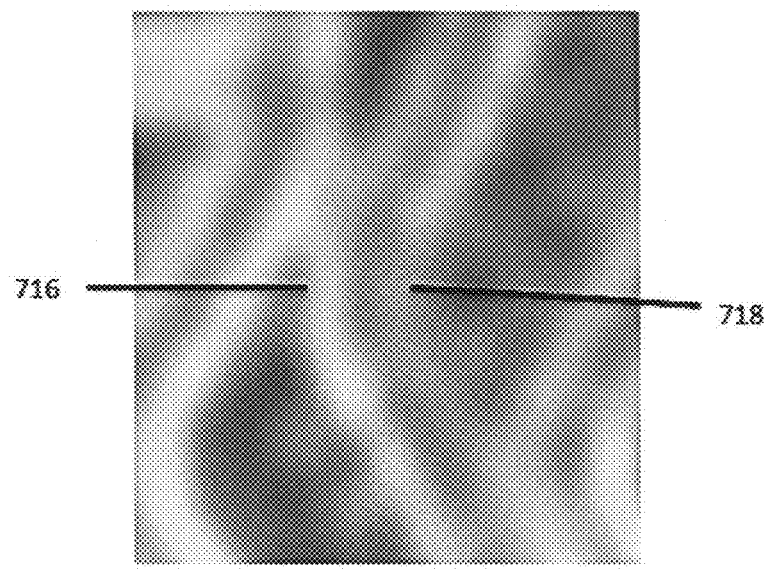
Figures 14A, 14B, 14C, 14D:
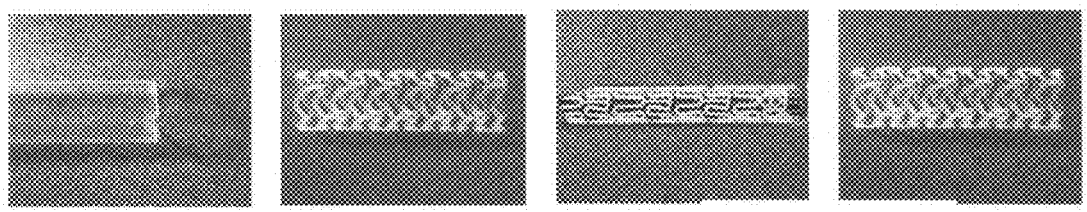
FIGS. 14A-D depict an expanded tube, a laser cut scaffold, a crimped scaffold, and a deployed scaffold, respectively.

FIG. 13A depicts an image of the sample scaffold 700. Scaffold 700 includes struts having an outer or abluminal surface that contacts a vessel wall when deployed, an inner or luminal surface that faces a vessel lumen when deployed, and sidewalls or sidewall surfaces between the abluminal and luminal surfaces. FIG. 13B depicts an enlarged image of the scaffold 700 of FIG. 13A illustrating the structure. The scaffold includes circumferential rings 702 connected by linking struts or bar arms 704. FIG. 13C depicts a further enlarged image of scaffold 700 of FIG. 13A illustrating the structure of the rings. The rings include bending elements that include strut sections or bar arms 712 and 714 that meet at a crest 706. Crest 706 is a free crest, meaning that it is not directly connected to any linking strut. The scaffold also includes W crests (e.g., crest 710) and Y crests (e.g., crest 708). Y crests are connected to a linking strut at an outer convex portion of the crest and a W crest is connected to a linking strut at an inner concave portion of the crest. The bending elements bend inward (e.g., strut sections 712 and 714 bend toward each other) when the scaffold is crimped and bend outward (i.e., strut sections 712 and 714 bend away from each other) when the scaffold is deployed or expanded from a crimped configuration. FIG. 13D depicts a further enlarged image of scaffold 700 of FIG. 13A illustrating the structure of a crest. A crest has an outer side, bend or edge 716 and an inner, side, bend or edge 718.

The scaffold samples were crimped at a temperature of about 48° C. onto a collapsed 3 mm balloon to between 0.051 to 0.055 in OD. The crimped scaffolds were e-beam sterilized and were pre-soaked for two minutes in 37° C. water prior to being deployed to 3 mm ID by expanding the balloon. FIGS. 14A-D depict an expanded tube, a laser cut scaffold, a crimped scaffold, and a deployed scaffold, respectively.

Sections for analysis by PLM and x-ray scattering were taken from the sample expanded tube and scaffold at various stages of the manufacturing process: as-cut, crimped, and deployed scaffolds. Sections were created to probe crystal structure and orientation as a function of radial (R) and azimuthal (θ) position. The spatial resolution of microstructure of the expanded tube was studied in the radial direction and the azimuthal direction.

Figure 15:
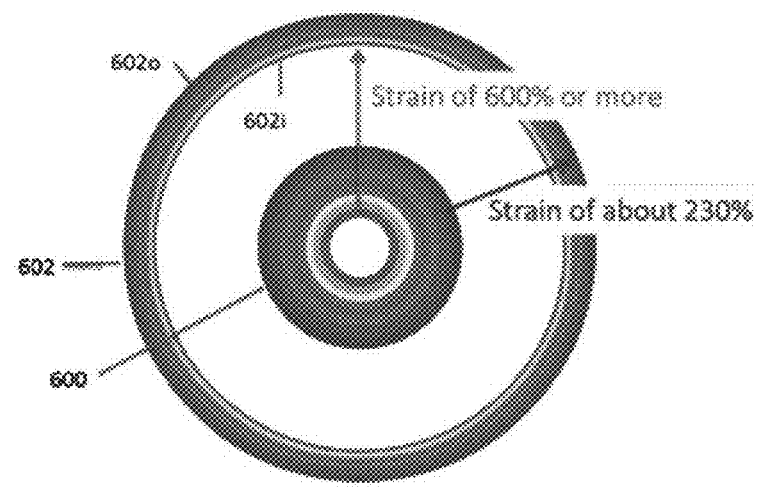
FIG. 15 depicts a tube prior to radial expansion and the tube after radial expansion.

During the expansion process the tube experiences both thermal nonuniformity and strain nonuniformity. The thermal nonuniformities are due to differences in thermal heating arising from the various mechanisms of heat transfer including radiation, conduction, and convection. The strain nonuniformity is illustrated in FIG. 15. FIG. 15 depicts a tube prior to radial expansion 600 and the tube after radial expansion 600. In the tube after expansion, the strain in the radial direction increases from the outside surface 602$o$ (least strain) to the inside surface 602$i$ (most strain). Each of the circular color bands in the tube prior to radial expansion 600 are the same radial thickness. In the tube after radial expansion 602, the thickness of the color bands decreases between the outside surface 602$o$ to the inside surface 602$i$. Strain nonuniformity may also arise in the azimuthal direction due to thermal nonuniformities.

The spatial resolution of microstructure of the expanded tube in the radial direction was obtained from radial sections of an as-cut scaffold sample. The radial thickness of the expanded tube used to generate the as-cut scaffold was about 160 microns. The radial sections cut from the axial section were 10 to 15 microns thick from the outside diameter (OD) to the inside diameter (ID).

Figure 17:
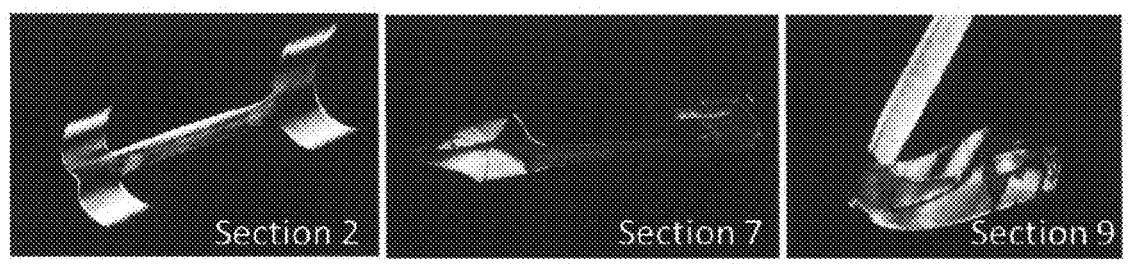
FIG. 17 depicts PLM images of three radial sections between the OD and the ID of the tube.

The radial sections were studied with PLM. A gradient in birefringence within the scaffold wall is seen in the PLM images. Sequential sections from OD to the ID show a transition from optically isotropic to birefringent at approximately 100 microns from the OD which is about ⅔ of the wall thickness. FIG. 17 depicts PLM images of three radial sections between the OD and the ID of the tube. Sections 2 and 7 show optical isotropy and section 9 shows birefringence. The optical isotropy indicates that there is no induced orientation from the radial expansion in this radial section. The birefringence of the inner radial section indicates induced polymer crystalline orientation.

It is believed that the absence of crystal orientation in the outer radial section may be due in part to the significant difference in radial strain experienced between ID and OD of the extruded tubing during expansion, as illustrated in FIG. 15.

It is believed that the absence of crystal orientation in the outer radial section may be due in part to the contact of the outer surface of the expanded tube with the heated glass mold when the tube is expanded. Contact with the mold may result in greater heat transfer into the polymer at the tube outer surface which allows for faster relaxation of polymer chains in the radial section closest to the mold.

It is believed that the processing conditions of the radial expansion process may be modified to vary the radial location of the gradient or transition of optically isotropic to birefringence or unoriented to oriented crystal structure. For example, the process may be modified so that the tube or struts have induced molecular orientation in a region greater than ⅓ or greater than ½ of the radial thickness from the inner surface with no induced orientation beyond the ⅓ or ½ of the radial thickness.

Figure 16:
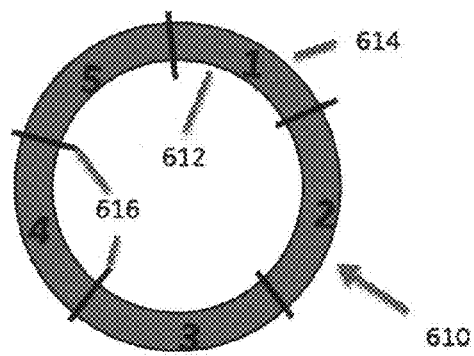
FIG. 16 depicts a radial cross-section of a ring cut from an expanded tube having an inner surface and outer surface.

Azimuthal sections of the expanded tube samples were examined with PLM and WAXD to assess the azimuthal variation in microstructure. WAXD was also used to assess the type of crystal structure. Azimuthal sections were prepared from a ring cut from expanded tubing which was cut into five azimuthal sections. The WAXD experiments were done at the ALS, Lawrence Berkeley National Lab. FIG. 16 depicts a radial cross-section of a ring cut from an expanded tube 610 having an inner surface 612 and outer surface 614. The ring is cut into five azimuthal sections 1 to 5 delineated by lines 616.

Figure 18:
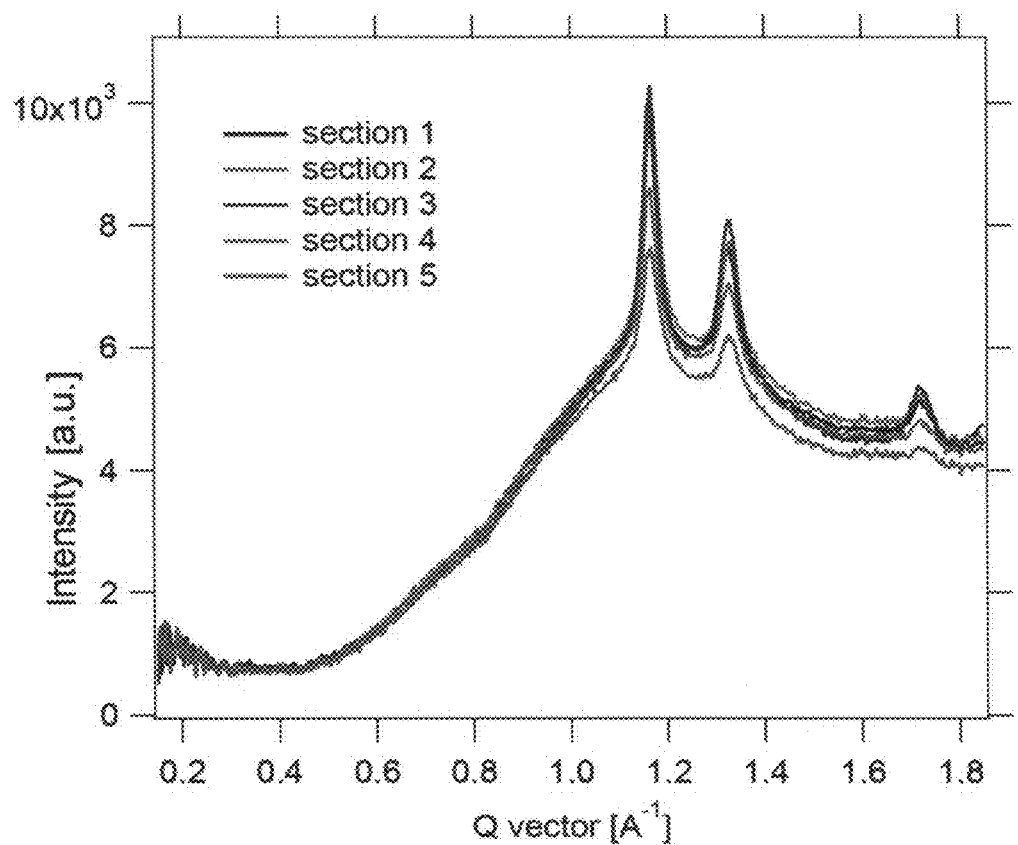
FIG. 18 depicts the 2-D WAXD patterns of the intensity vs. q vector of the five azimuthal sections of FIG. 16.

FIG. 18 depicts the 2-D WAXD patterns of the intensity vs. q vector of the five azimuthal sections of FIG. 16. FIG. 18 shows that the degree and the direction of orientation of the crystallites is consistent, indicating azimuthal uniformity. Degree of orientation is a function of diffraction spot size, while direction is a function of diffraction spot location. The plot also shows the relative proportions of crystalline to amorphous domains by characterizing the relative peak heights and the amorphous background halo, which is the very broad peak of a diffraction pattern due to amorphous domains.

Figure 19:
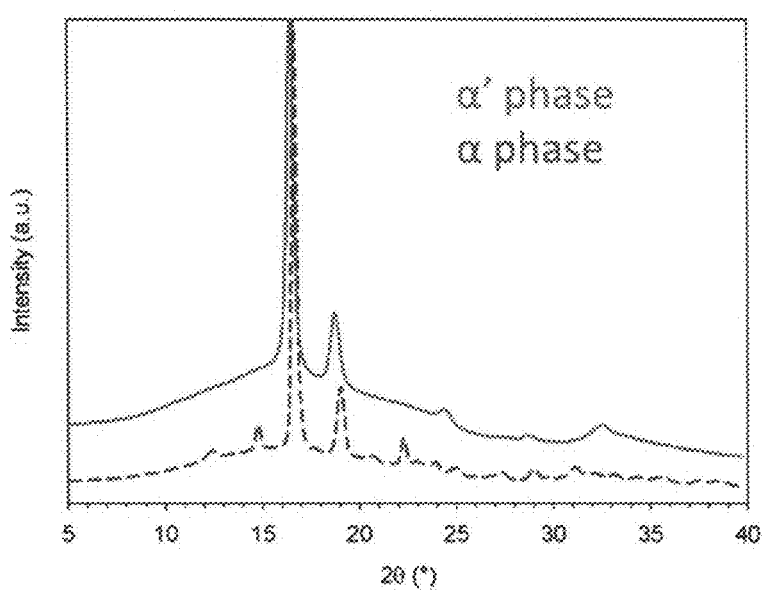
FIG. 19 shows a 1-D WAXD pattern from the literature showing differences between a and α' crystal structures.

FIG. 18 further shows that only α' crystal structure is detectable in the crystallites of the sections of tube. FIG. 19 shows a 1-D WAXD pattern from the literature showing differences between α and α' crystal structures. Macromolecules, Vol. 43, No. 3, 2010.

Figure 20:
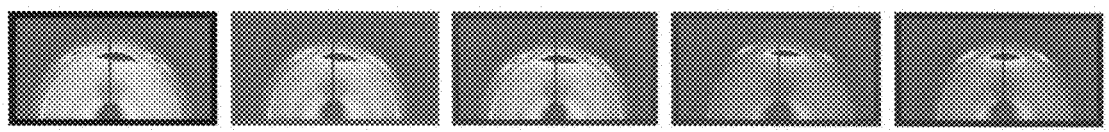
FIG. 20 shows 2-D and 1-D WAXD patterns of the sections 1 to 5 of FIG. 16 from left to right illustrating the azimuthal uniformity of α' crystal structure of the expanded tube.

The WAXD patterns of the azimuthal sections further show azimuthal uniformity of the α' crystal structure. FIG. 20 shows 2-D and 1-D WAXD patterns of the sections 1 to 5 of FIG. 16 from left to right illustrating the azimuthal uniformity of α' crystal structure of the expanded tube in terms of consistent diffraction spot size and position.

The impact of crimping on the microstructure of the bends or crests of the scaffold was assessed by PLM and WAXD. The PLM images of the crests are radial sections parallel to the luminal and abluminal surfaces that are about 90 to 100 microns from the abluminal surface of the scaffold. Therefore, the radial sections are near or closer to the luminal surface.

Figure 21:
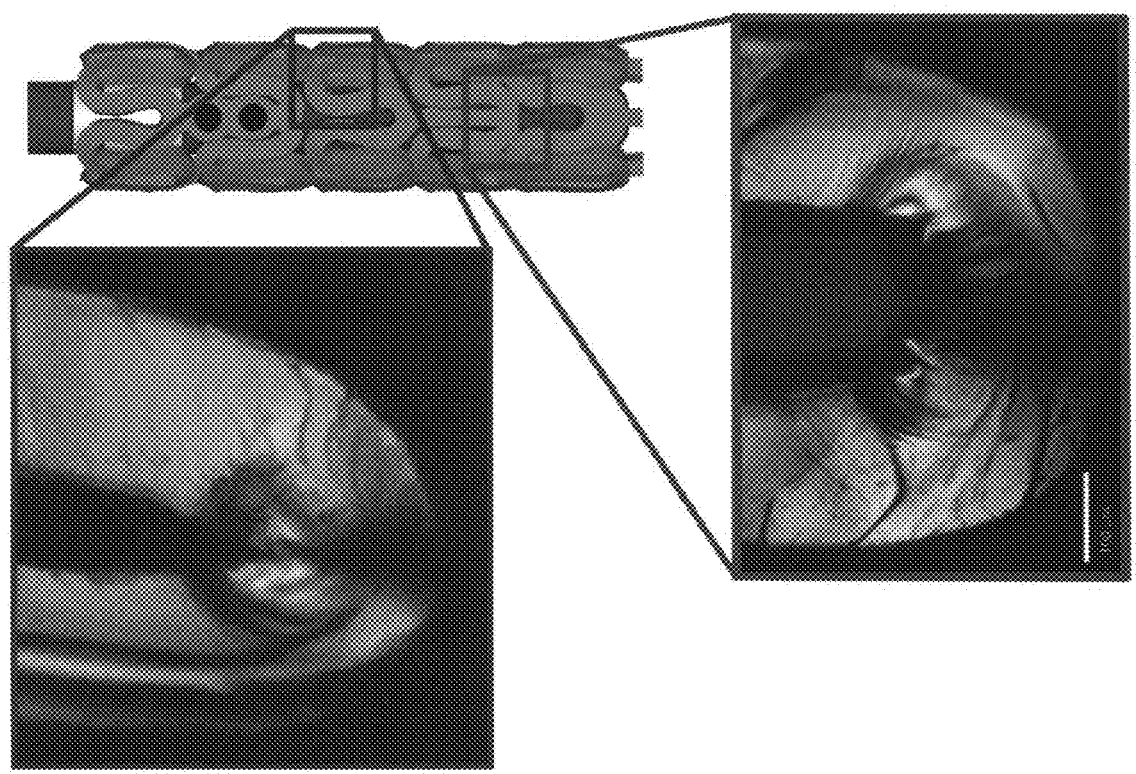
FIG. 21 depicts a crimped scaffold and two PLM images of radial sections of a free crest and a W crest.
Figure 22A:
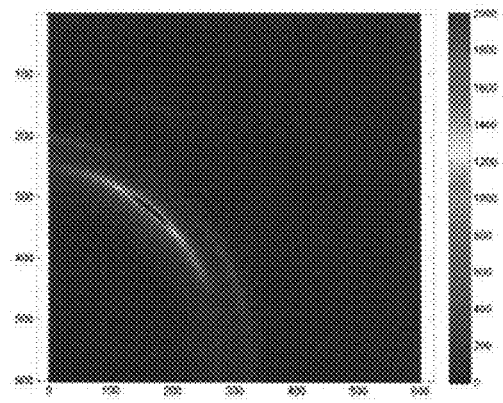
FIGS. 22A-22 Ddepict WAXD patterns of radial sections of a free crest in regions at or adjacent to the outer edge and the inner edge of the crest, respectively.
Figure 22B:
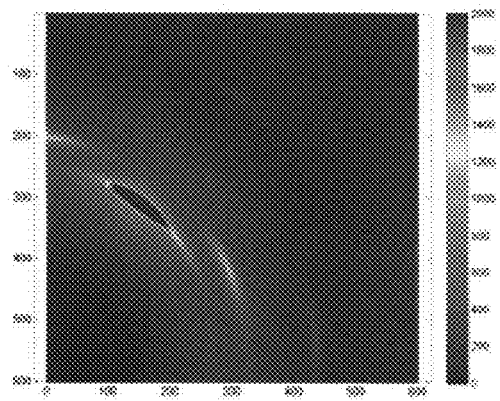
Figure 22C:
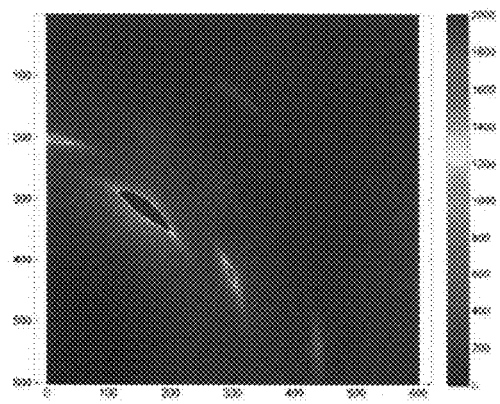

FIG. 21 depicts a crimped scaffold and two PLM images of radial sections near the luminal surfaces of a free crest and a W crest. When the scaffold is crimped there is significant tension on the outer edge or bend region of a crest and compression at the inner bend or edge region of the crest. The images show high retardance at the outer region of the crests, indicative of strong orientation in the azimuthal direction induced during the crimping process. Therefore, the orientation at the outer edge and region adjacent in the crimped scaffold is higher than the struts which remain undeformed.

However, the induced orientation varies between the inner edge and the outer edge of the crest. The images further show a smaller change in orientation or a less significant induced orientation due to crimping at the inner edge and region adjacent of the crests. Therefore, in the crimped scaffold there is an increase in orientation between the inner bend and the outer bend of the crimped scaffold, as evidenced by the increase in retardance when moving from the inner bend to the outer bend in the PLM image It is believed that high retardance at or adjacent to the outer edge of the crest may be due to one or more of induced orientation of amorphous polymer, reoriented crystallites, and new crystallites induced during the deformation of the crimping process.

WAXD patterns of a radial section of a free crest were obtained at four locations of a radial section: the inner edge, outer edge, and two locations between the inner edge and outer edge of the crest. FIGS. 22A-22D depict the WAXD patterns of the locations between the outer edge and the inner edge, respectively. FIGS. 22A-D show an increase in local crystallinity and degree of orientation moving from the inner edge to the outer edge. No induced orientation was observed for the pattern at the inner edge, however, induced orientation was observed in the three other patterns. Additionally, the WAXD patterns show that there was no change in $\alpha'$ crystal structure induced by the crimping.

Additionally, shear or yield bands are detectable from the PLM images at or adjacent to the inner edge of the crimped scaffold, in particular for the W crest in FIG. 21. A shear band (or a strain localization or localized deformation) is a narrow zone of intense shearing strain, usually of plastic nature, developing during severe deformation of a material. Shear bands are observed in ductile materials and are not typically observable in brittle materials (for instance a polymer below its Tg). The shear banding phenomena may precede failure, since extreme deformations occurring within shear bands may lead to damage and fracture. The inner edge has fissures or crazing at the inner edge of the crest visible on the sidewalls of the inner edge of the crest.

The PLM images further show that the chain axis orientation and degree of orientation are dependent on position relative to inner and outer crests. The optical path difference is higher near the outer edge of the crest relative to the inner edge. While both are birefringent, the stronger signal near the outer edge implies more highly oriented material in this region.

FIGS. 23A-D depict images of samples of an expanded tube, as-cut scaffold, crimped scaffold, and deployed scaffold with an overlay of the initial (tube and as-cut scaffold) azimuthal chain orientation (arrows) and the WAXD reflection orientation of 200/110 crystal (dumbbells). As shown, when the scaffold is crimped and deployed the polymer chain orientation and WAXS diffraction spot positions change relative to the longitudinal axis of the scaffold. Therefore, the direction of the observed orientation depends on the state of the scaffold: as-cut, crimped, or deployed.

Figure 24:
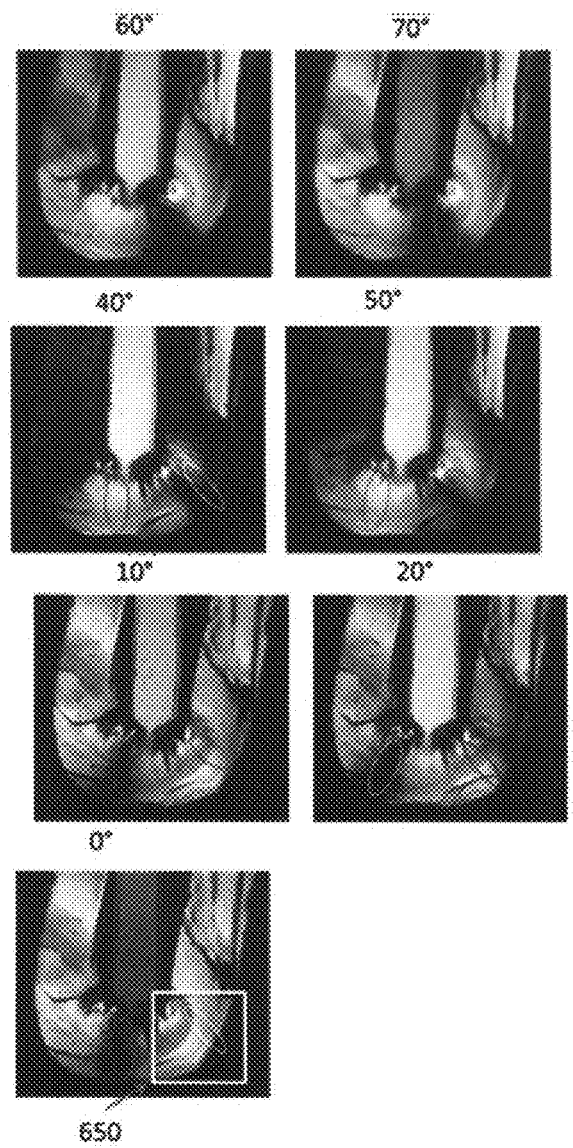
FIG. 24 depicts PLM images of a W crest of a crimped scaffold at different rotational positions of the polarizer.

FIG. 24 depicts PLM images of a W crest of a crimped scaffold at different angles of the polarizer filter between 0° and 70°. To estimate the retardance at a given point the sample is rotated 45° with respect to orientation at which the point appears dark. For the white oval, extinction takes place with the polarizers at about 45°. The retardance is thus determined by the image taken with the polarizers in line with each other, with the angle of 0°. The link strut extending from the inner edge is not deformed during crimping, and therefore, has the same orientation as the expanded tube and the uncrimped scaffold. Its retardance does not change with rotation of the polarizing filters.

Figure 25:
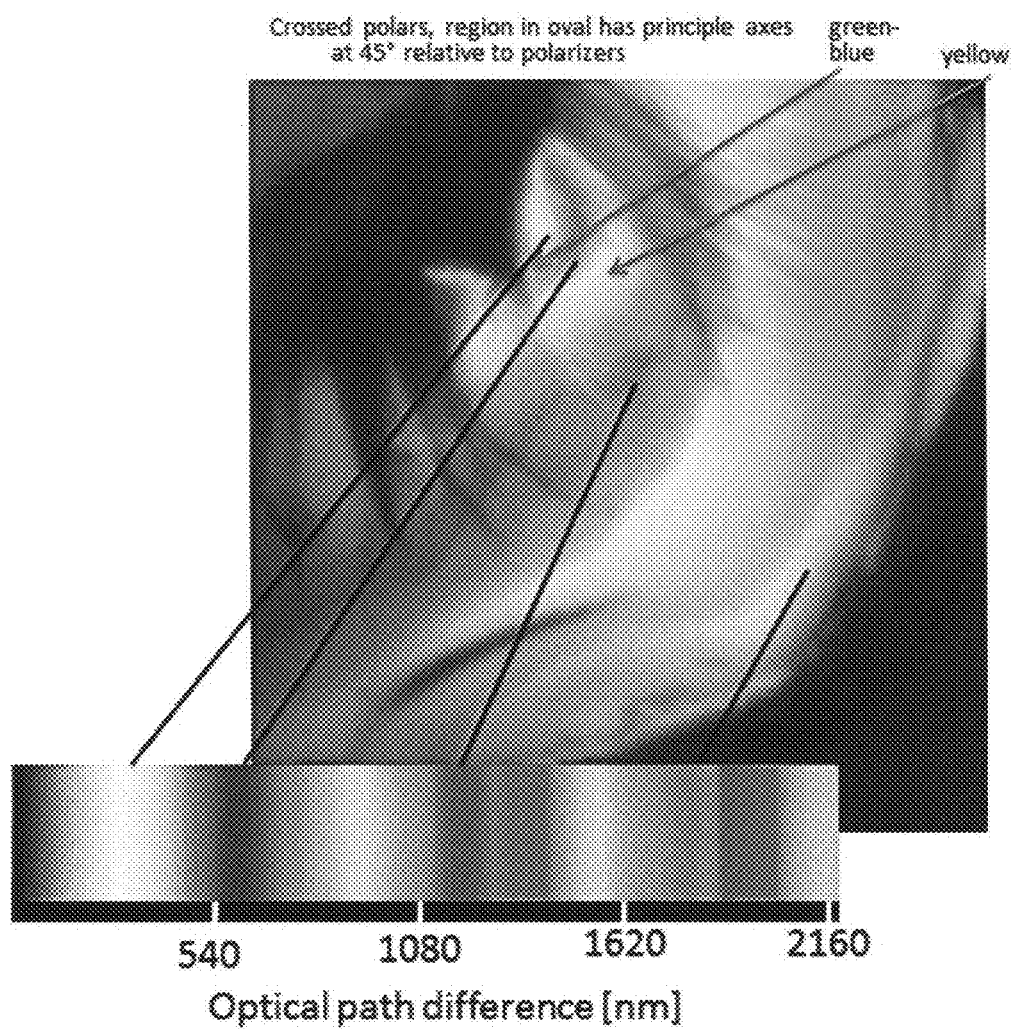
FIG. 25 depicts a region in FIG. 24 in detail including a section enclosed by an oval from the region having a principal axis at 45° relative to the polarizing filter.

FIG. 25 depicts region 650 in FIG. 24 in detail. The region in the oval from region 650 in FIG. 24 has a principal axis at 45° relative to the polarizers. The color bands from the Michel-Levy color scale shown are assigned to the color bands that radiate from the inner edge to the outer edge of the crest, which is from the upper left to the lower right of FIG. 25.

Figure 26:
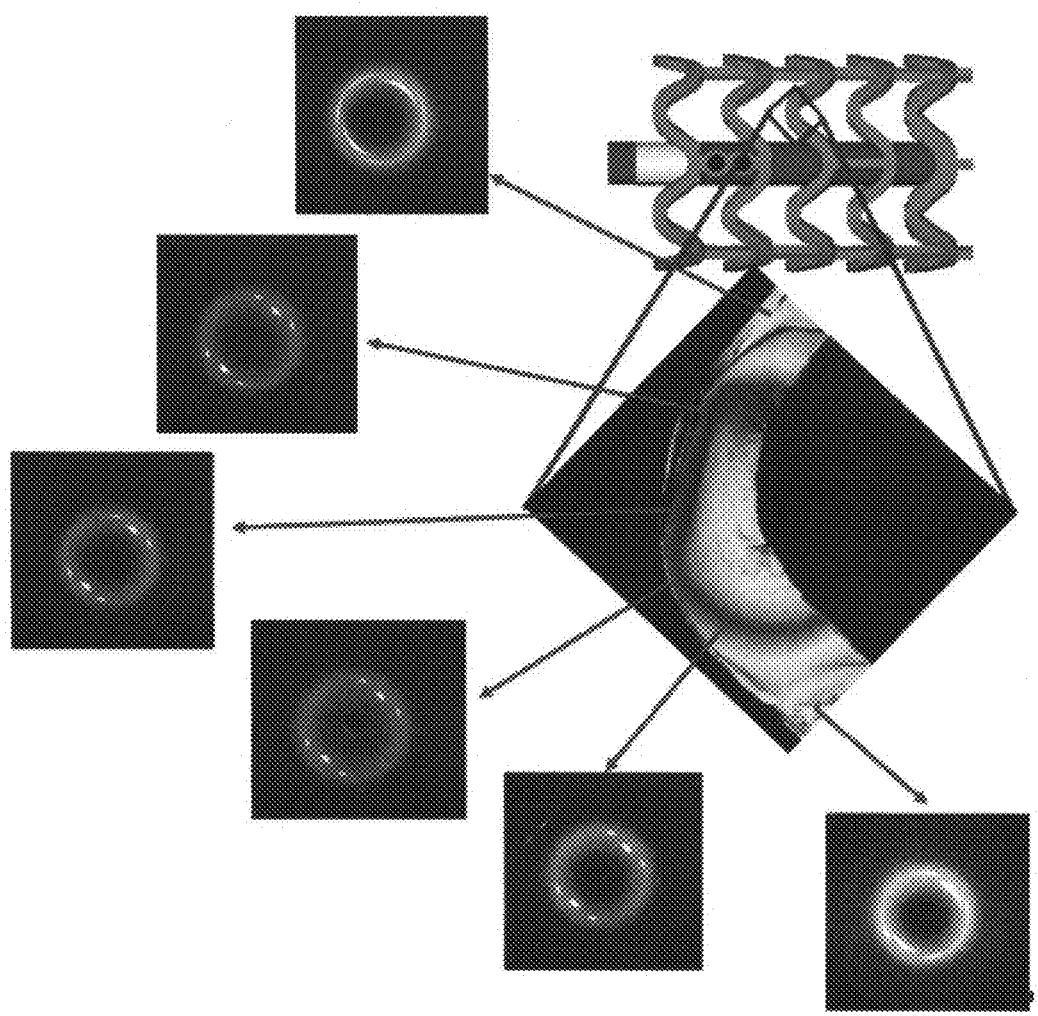
FIG. 26 depicts a deployed scaffold and a PLM image of radial sections of a free crest and 2-D WAXD patterns from locations along the outer edge or bend of the crest between strut sections or bar arms.

The impact of deployment on the microstructure of the bends or crests of the scaffold was examined by PLM and WAXD. FIG. 26 depicts a deployed scaffold and a PLM image of luminal sections of a free crest and 2-D WAXD patterns from locations along the outer edge or bend of the crest between the strut sections that meet at the crest. When the scaffold is deployed there is compression on the outer or convex edge of the crest and tension at the inner or concave edge of the crest.

The 2-D WAXD patterns of FIG. 26 show azimuthal orientation changes, i.e., increases, between the strut sections and high stress regions on the outer edge of the crest. The combination of the PLM image and the 2-D WAXD patterns shows the consistency of orientation within a color band. The images show that deployment does not induce a change in orientation within strut sections and that the outer crest retains the high degree of orientation induced by crimping. The outer crests are under compression, but the material in this region has developed properties of low compressibility and higher stiffness due to the increased orientation making it harder to deform. No crazing or fracture was observed at the outer edge of the crest in the crimped or deployed states. It is believed that the highly oriented polymer at and adjacent to the outer edge acts as a barrier to crack propagation to the outer edge.

As indicated above, the crimped scaffold exhibits crazing or has craze regions at the inner edge of the crests. When the scaffold is deployed, it is believed that tension on inner crests is relieved by the surface craze regions which grow into "diamond-shaped voids" during deployment. Polymer at the inner crest is still weakly oriented, however, highly oriented fibrils form within the crazed regions upon deployment.

As indicated above, WAXD patterns show that there was no change in $\alpha'$ crystal structure induced by the crimping. Additionally, there was no change in $\alpha'$ crystal structure induced by the deployment. $\alpha'$ crystal structure is less ordered than $\alpha$ crystal structure, therefore, it is believed that $\alpha'$ crystal structure has a higher resistance to fracture due to the ability Of the disordered lattice to dissipate stress. It is believed that resistance to failure on deployment is enhanced by the presence of $\alpha'$ rather than $\alpha$ crystal structure in the outer crest.

Figure 27:
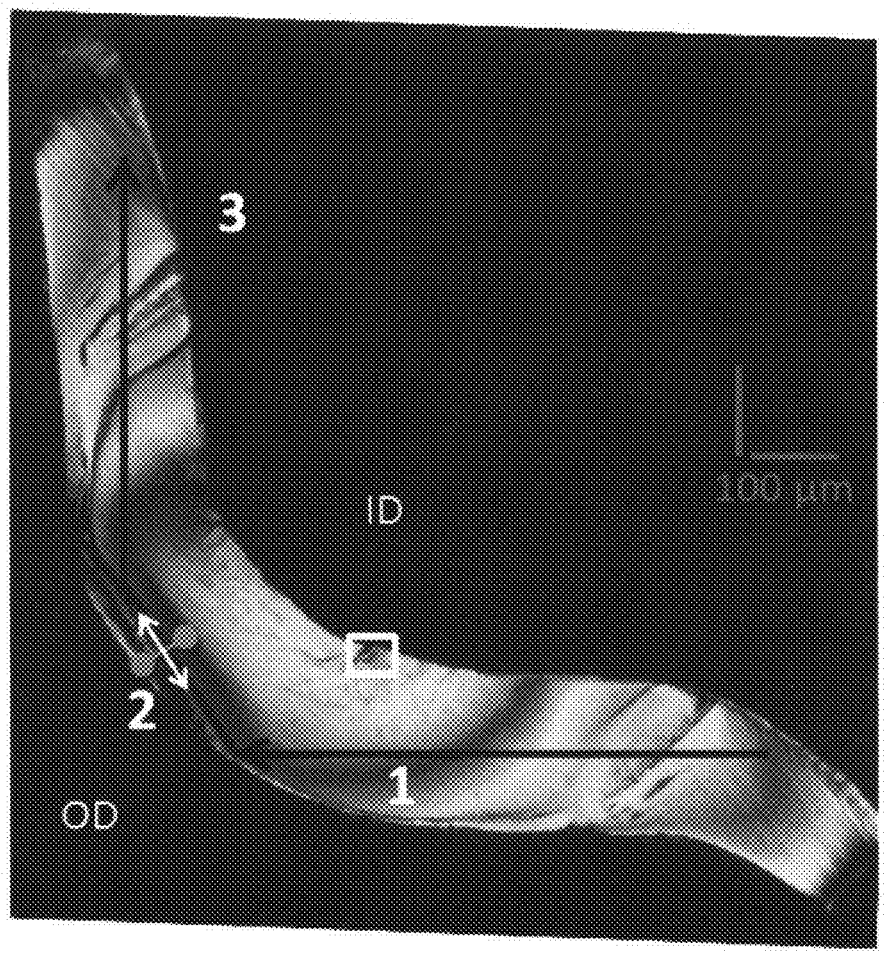
FIG. 27 depicts the PLM image of FIG. 26 showing a larger portion of the crest and strut sections.

FIG. 27 depicts the PLM image of FIG. 26 showing larger portion of the crest and strut sections. Arrows 1, 2, and 3 show the path of the WAXD microdiffraction beam for three scans. Due to beam damage, the beam path looking at the sample under the microscope can be observed. Line scan 1 is from a region of low retardance to high retardance. Line scan 2 is along the outer edge of the crest where crimping induces very high retardance. Line scan 3 is the reverse of scan 1, from high to low retardance. The PLM image shows the chain orientation (arrow) and the WAXD reflection orientation of 200/110 crystal (dumbbell).

Figure 28:
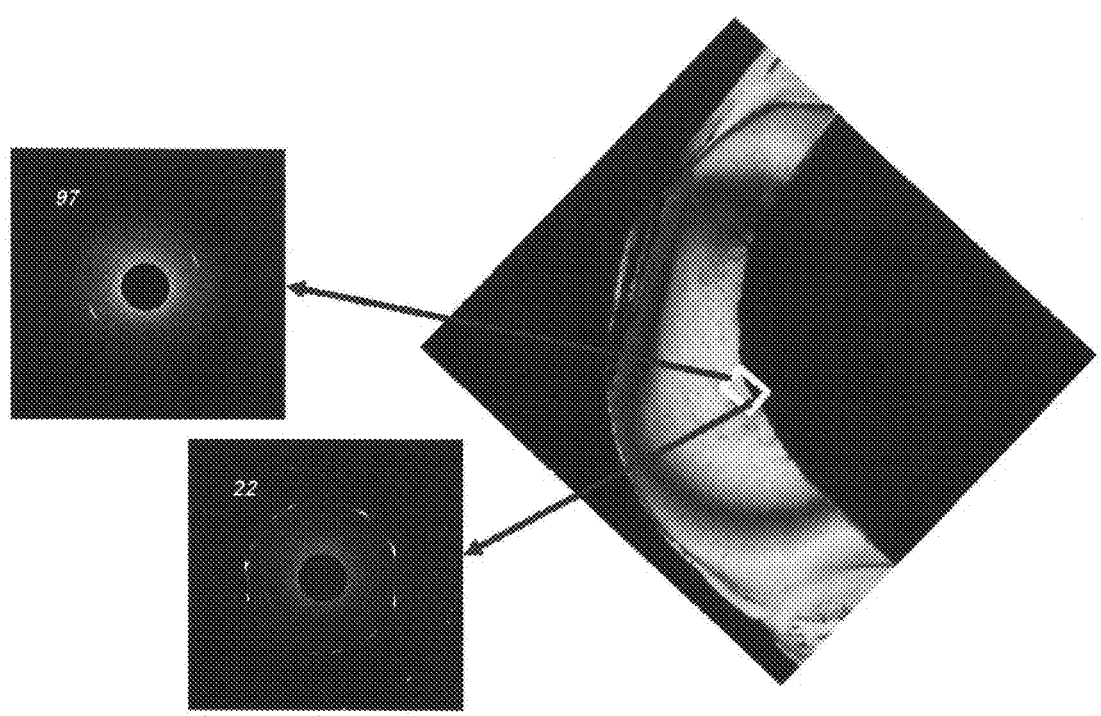
FIG. 28 depicts the PLM image of the FIGS. 26 and 2-D WAXD patterns showing weakly oriented PLLA in the inner edge of the crest adjacent to highly oriented fibrils within a craze.

FIG. 28 depicts the PLM image of the FIGS. 26 and 2-D WAXD patterns showing weakly oriented PLLA in the inner edge of the crest adjacent to highly oriented fibrils within a craze.

Figure 29A:
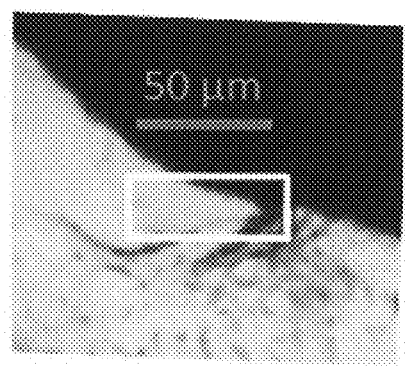
FIG. 29A depicts close-up view of the PLM image of the inner edge of FIG. 28.
Figure 29B:
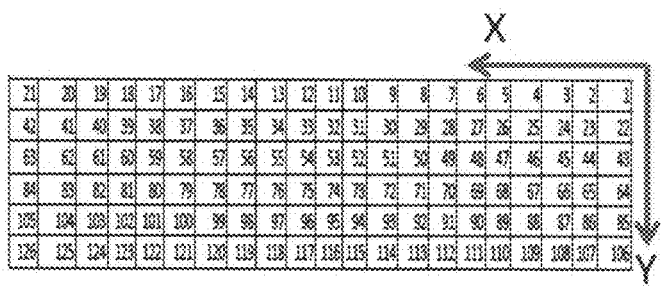
FIG. 29B depicts a grid of sections of the delineated region of FIG. 29A scanned by WAXD.

FIG. 29A depicts close-up view of the PLM image of the inner edge of FIG. 28 with a 50 micron region delineated. FIG. 29B depicts a grid of sections of the delineated region of FIG. 29A scanned by WAXD. Sections 97 is included in FIG. 29 showing the two diffraction spots of weakly oriented crystals. Section 22 represents a fibrillated craze and the diffraction pattern in FIG. 29 shows many pairs of diffraction spots consistent with randomly oriented fibrils.

Figure 30:
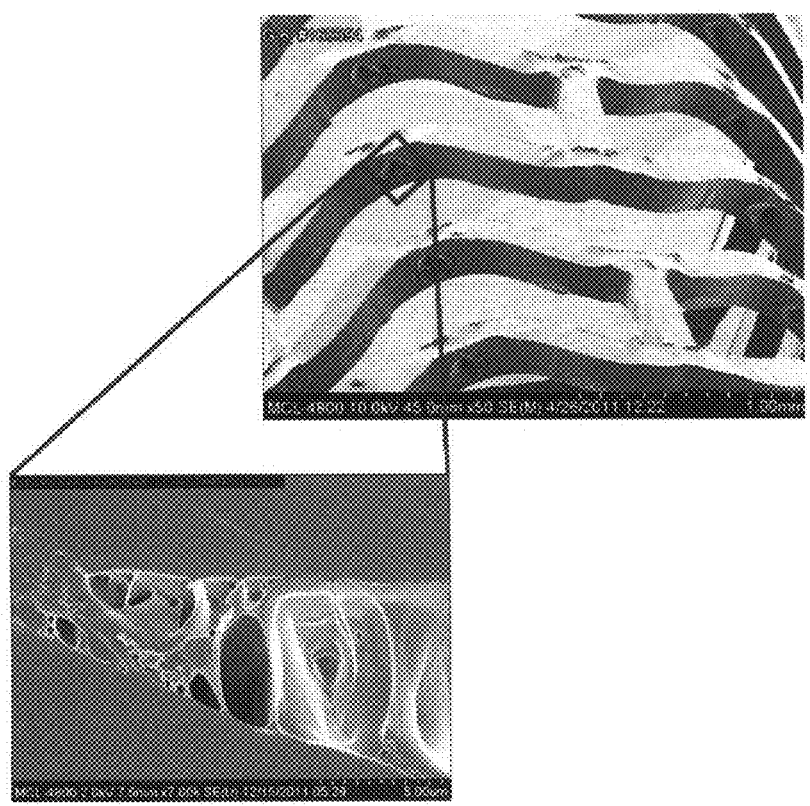
FIG. 30 depicts an SEM image of a deployed scaffold and an SEM image at a higher resolution of a cross-section of an inner edge of a crest.

FIG. 30 depicts an SEM image of a deployed scaffold and an SEM image at a higher resolution of the cross-section of an inner edge of a crest. The high resolution image shows a diamond-shaped void region and fibrils within a crazed region.

The examples and experimental data set forth above are for illustrative purposes only and are in no way meant to limit the invention. The following examples are given to aid in understanding the invention, but it is to be understood that the invention is not limited to the particular materials or procedures of examples.

U.S. Patent Publication Nos. 2007/0282433, 2011/0270383, 2008/0275537 are incorporated by reference herein for all purposes.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A biodegradable stent comprising:
a scaffold including struts comprising a poly(L-lactide)-based biodegradable polymer, wherein the struts have a luminal surface and an abluminal surface, wherein the polymer has induced polymer orientation in a circumferential direction, and wherein the induced polymer orientation decreases from the luminal surface to the abluminal surface of the struts, wherein the polymer has the induced polymer orientation in a radial section between the luminal surface and a transition radial distance and no induced polymer orientation between the transition radial distance and the abluminal surface, and wherein the transition radial distance is ⅓ to ½ of a radial thickness of the struts.

2. The stent of claim 1, wherein the scaffold is formed by cutting a pattern in a radially expanded tube having the induced polymer orientation that was induced by radially expanding the tube.

3. The stent of claim 1, wherein a degree of the induced polymer orientation is uniform around a circumference of the scaffold.

4. A biodegradable stent comprising:
a scaffold including struts comprising a poly(L-lactide)-based biodegradable polymer, wherein the struts have a luminal surface and an abluminal surface, and wherein a luminal radial section of the struts exhibits birefringence and an abluminal radial section is optically isotropic when viewed with polarized light, wherein the luminal radial section has a thickness that is ⅓ to ½ of a radial thickness of the struts from the luminal surface to the abluminal surface.

* * * * *

UNITED STATES PATENT AND TRADEMARK OFFICE
CERTIFICATE OF CORRECTION

Page 1 of 1

PATENT NO. : 9,517,149 B2
APPLICATION NO. : 13/998199
DATED : December 13, 2016
INVENTOR(S) : Gale et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*